United States Patent
Hamann et al.

(10) Patent No.: US 6,995,183 B2
(45) Date of Patent: Feb. 7, 2006

(54) ADAMANTYLGLYCINE-BASED INHIBITORS OF DIPEPTIDYL PEPTIDASE IV AND METHODS

(75) Inventors: Lawrence G. Hamann, Cherry Hill, NJ (US); Ashish Khanna, Ambler, PA (US); Mark S. Kirby, New Hope, PA (US); David R. Magnin, Hamilton, NJ (US); Ligaya M. Simpkins, Titusville, NJ (US); James C. Sutton, Princeton Junction, NJ (US); Jeffrey Robl, Newtown, PA (US)

(73) Assignee: Bristol Myers Squibb Company, Princeton, NJ (US)

(*) Notice: Subject to any disclaimer, the term of this patent is extended or adjusted under 35 U.S.C. 154(b) by 122 days.

(21) Appl. No.: 10/899,641

(22) Filed: Jul. 27, 2004

(65) Prior Publication Data

US 2005/0038020 A1 Feb. 17, 2005

Related U.S. Application Data

(60) Provisional application No. 60/491,832, filed on Aug. 1, 2003.

(51) Int. Cl.

| | | |
|---|---|---|
| A61K 31/403 | (2006.01) | |
| A61K 31/426 | (2006.01) | |
| A61K 31/4453 | (2006.01) | |
| C07D 209/52 | (2006.01) | |
| C07D 205/04 | (2006.01) | |
| C07D 295/00 | (2006.01) | |
| C07D 279/12 | (2006.01) | |
| C07D 259/03 | (2006.01) | |
| C07D 221/00 | (2006.01) | |
| C07D 295/16 | (2006.01) | |

(52) U.S. Cl. ............. 514/412; 514/210.01; 514/227.5; 514/231.2; 514/299; 514/319; 514/367; 514/374; 544/59; 544/106; 546/112; 546/195; 548/200; 548/215; 548/452; 548/528; 548/953

(58) Field of Classification Search .......... 544/59, 544/106; 546/112, 195; 548/200, 215, 452, 548/528, 953; 514/210.01, 227.5, 231.2, 514/299, 319, 367, 374, 412

See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |

(Continued)

FOREIGN PATENT DOCUMENTS

| | | |
|---|---|---|
| WO | WO 86/03488 | 6/1986 |
| WO | WO 86/07054 | 12/1986 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/34241 | 6/2000 |
| WO | WO 03/000250 | 1/2001 |
| WO | WO 01/81337 | 11/2001 |
| WO | WO 01/68603 A2 | 9/2002 |
| WO | WO 02/076450 | 10/2002 |
| WO | WO 03/002530 | 1/2003 |
| WO | WO 2004/052850 A2 | 6/2004 |

OTHER PUBLICATIONS

Wang, et al., "Effect of Vanadium on Insulin and Leptin in Zucker Diabetic Fatty Rats," Molecular and Cellular Biochemistry, vol. 218 pp. 93–96 (2001).*

Wrenger et al., "Down-regulation of T Cell Activation following Inhibition of Dipeptidyl Peptidase IV/CD26 by the N-terminal Part of the Thromboxane A2 Receptor," Journal of Biological Chemistry, vol. 275, No. 29, pp. 22180–22186 (2000).*

(Continued)

*Primary Examiner*—Joseph McKane
*Assistant Examiner*—Andrew Freistein
(74) *Attorney, Agent, or Firm*—Jonathan N. Provoost

(57) ABSTRACT

Compounds are provided having the formula (I)

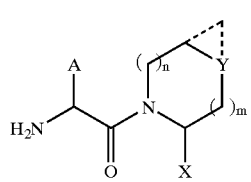

wherein:

n is 0, 1 or 2;

m is 0, 1 or 2;

the sum of n+m less then or equal to 2;

the dashed bonds forming a cyclopropyl ring can only be present when Y is CH;

X is H or CN;

Y is CH, $CH_2$, CHF, $CF_2$, O, S, SO, or $SO_2$; and

A is adamantyl.

Further provided are methods of using such compounds for the treatment of diabetes and related diseases, and to pharmaceutical compositions containing such compounds.

7 Claims, No Drawings

U.S. PATENT DOCUMENTS

| | | | |
|---|---|---|---|
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,346,701 A | 9/1994 | Heiber et al. |
| 5,354,772 A | 10/1994 | Kathawala |
| 5,385,929 A | 1/1995 | Bjorge et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,595,872 A | 1/1997 | Wetterau, II et al. |
| 5,612,359 A | 3/1997 | Murugesan |
| 5,614,492 A | 3/1997 | Habener |
| 5,631,224 A | 5/1997 | Efendic et al. |
| 5,686,104 A | 11/1997 | Mills et al. |
| 5,691,322 A | 11/1997 | Robl |
| 5,712,279 A | 1/1998 | Biller et al. |
| 5,712,396 A | 1/1998 | Magnin et al. |
| 5,739,135 A | 4/1998 | Biller et al. |
| 5,753,675 A | 5/1998 | Wattanasin |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,939,560 A | 8/1999 | Jenkins et al. |
| 5,962,440 A | 10/1999 | Sulsky |
| 6,043,265 A | 3/2000 | Murugesan et al. |
| 6,110,949 A | 8/2000 | Vilhauer |
| 6,395,767 B2 | 5/2002 | Robl et al. |
| 6,414,002 B1 | 7/2002 | Cheng et al. |

OTHER PUBLICATIONS

A Textbook of Drug Design and Development, P. Krogsgaard–Larson and H. Bundgaard, eds. Ch 5, pp. 113–191 (Harwood Academic Publishers, 1991).

Ahren et. al., Journal of Clinical Endocrinology & Metabolism 2004, 89 (5) pp. 2078–2084 Inhibition of Dipeptidyl Peptidase–4 Reduces Glycemia, Sustains Insulin Levels, and Reduces Glucagon Levels in Type 2 Diabetes.

Asworth et. al., Bioorg. & Med. Chem. Lett., vol. 6, No. 10, pp. 1163–1166, 1996 "2–Cyanopyrrolidides as Potent, Stable Inhibitors of Dipeptidyl Peptidase IV".

Ashworth et, al., Bioorg. & Med. Chem. Lett., vol. 6, No. 22, pp. 2745–2748, 1996 "4–Cyanothiazolidides as very Potent, Stable Inhibitors of Dipeptidyl Peptidase IV".

Balkan et. al., Diabetologia 1999, 42 (11), 132. "Inhibition of dipeptidyl peptidase IV with NVP–DPP728 increases plasma GLP–1 (7–36 amide) concentrations & improves oral glucose tolerance in obese Zucker rats".

Biller et. al., Current Pharmaceutical Design, 2, 1–40 (1996) "Squalene Synthase Inhibitors".

Biller et. al., Journal Medicinal Chemistry, 1988, vol. 31, No. 10, pp. 1869–1871 "Isoprenoid (Phosphinylmethyl) phosphonates as Inhibitors of Squalene Synthetase".

Capson, T. L., PhD, Dissertation, Jun., 1987, Dept. Med. Chem. U of Utah, abstract, Table of Contents, pp. 16, 17, 40–43, 48–51, Summary Synthesis and Evaluation of Ammonium Analogs of Carbocationic Intermediates in Squalene.

Corey and Volante, Journal of American Chemistry Society, 1976, 98(5), pp. 1291–1293 Application of Unreative Analogs of Terpenoid Pyrophosphates to Studies fo Multistep Biosynthesis. Demonstration That "Presqualene Pyrophosphate" is an Essential Intermediate on the Path to.

Cornicelli et. al., Current Pharmaceutical Design, 1999, 5, 11–20 "15–Lipoxygenase andits Inhibition: A Novel Therapeutic Target for Vascular Disease".

Design of Prodrugs, edited by H. Bundgaard, (Elsevier, 1985), Table of Contents.

Drugs of the Future 1999, 24(1), pp 9–15 "Avasimibe".

Drugs of the Future, 1999, 24(4), pp. 425–430 "Ileal Na+/bile acid cotransporter inhibitors".

"The pharmacological profile of FCE 27677: a novel ACAT inhibitor with potent hypolipidemic activity medicated by selective suppression of the hepatic secretion of ApoB100–containing Lipoprotein", Ghiselli, Giancarlo, Cardiovasc. Drug Rev. (1998); 16(1), pp. 16–30.

Hanessian et. al., Bioorganic & Medicinal Chemistry Letters, 1998; 8, pp. 2132–2128 "Probing the Importance of Spacial and Conformational Domins in Captopril Analogs for Angiotensin Converting Enzyme Activity".

Holst, J. J and Deacon, C. F., Diabetes, 1998, (47), pp. 1663–1670. "Inhibition of the activity of Dipeptidyl–Peptidase IV as a Treatment for TYP Diabetes".

Johannsson et. al., Journal of Clinical Endocrinol and Metabolism, vol. 82, pp 727–34 (1997) "Growth Hormane Treatment of Abdominally Obese Men Reduces Abdominal Fat Mass, Improves Glucose and Lipoprotein Metabolism, & Reduces Diastolic blood Pressure".

Krause et. al., Inflammation: Mediators Pathways (1995), 173–98, Publisher: "ACAT Inhibitors: physiologic mechanisms for hypolipdemic and anti–atherosclerotic activities in experimental animals".

McClard et al., Journal American Chemical Society, 1987, 109, pp. 5544–5545 Novel Phosphonylphosphiny (P–C–P–C) analogues of Biochemically Interesting Diphosphates. Syntheses and Properties of P–C–P–C Analogues of Isopentenyl Diphosphate & Dimethylally . . . .

McIntosh, C.H.S.; Pederson, R.A.; "Noninsulin–Dependent Animal Models of Diabetes Mellitus. In Experimental Models of Diabetes". Edited by John H. McNeill, CRC Press LLC, 1999, 337–398.

Murakami Koji et. al., Diabetes, (1998) 47, pp. 1841–1847 "A Novel Insulin Sensitizer Acts as a Coligand for Peroxisome Proliferator–Activated Receptor-a (PPAR–a) and PPAR–y".

Nagatsu et. al., Analytical Biochemistry (1976), 74, pp. 466–476 New Chromogenic Substrates for X–Prolyl Dipeptidy–Aminopeptidase.

Nicolosi et. al., Atherosclerosis (Shannon Irel), (1998)m 137(1), pp. 77–85 The ACAT inhibitor, Cl–1011 is effective in the prevention and regression of aortic fatty streak area in hamsters.

Ortiz de Montellano et. al., Journal of Medicinal Chemistry, 1977, vol. 20 (2), pp 243–249 "Inhibition of Squalene Synthetase by Farnesyl Pyrophosphate Analogues[1]".

Pauly et. al., Metabolism, Clinical and Experimental (1999), 48(3), pp. 385–389 "Improved Glucose tolerance in rats treated with the Dipeptidyl Peptidase IV (CD26) inhibitor lle–Thiazolidide".

Rosenblum et. al., J. Med. Chem., 41, pp 973–980 (1998) "Discover of 1-(4–Fluorophenyl)-(3R)-[3-(4–fluorophenyl)-(3S)-hydroxypropyl]-(4S)-(4-hydroxyphenyl)-2-azetidinone (SCH 58335): A Designed, Potent, Orally Active Inhibitor of . . . ".

Rahfeld, J. (1991) Biol. Chem. Hoppe–Seyler, 372, pp. 313–318 Extended Investigation of the Substrate Specificity of Dipeptidy Peptidase IV from Pig Kidney.

Rothenberg, P.; Diabetes 2000, 49(1) A39 "Treatment with a DPP–IV Inhibitor, NVP–DPP728, Increases Prandial Intact GPL–1 Levels and Reduces Glucose Exposure in Humans".

Sagnard et. al., Tetrahedron Lett., 1995, 36, pp. 3148–3152 "Enantioselective Synthesis of Cyclopropane a–Amino Acids: Synthesis of N–Boc–cis-(2S,3R,4S)–3,4–Methanoproline and N–Boc-(2S,3R,4S)–3,4–Methanoglutamic Acid".

Salisbury et. al., Atherosclerosis 115, 45–63 (1995) Hypocholesterolemic activity of a novel inhibitor of Cholesterol absorption, SCH 48461.

Schecter et. al., Biochem. Biophys. Res. Commun. 1967, 27(2) pp. 157–162 "On the Size of the Active Site in Proteases".

Sendobry et. al., British Journal of Pharmacology (1997) 120, pp. 1199–1206, "Attenuation of diet–induced atherosclerosis in rabbits with a highly selective 15–lipoxygenase inhibitor lacking significant antioxidant properties".

Sliskovic et al, Curr. Med. Chem. (1994), 1(3), pp. 204–225 "ACAT Inhibitors: Potential Anti–atherosclerotic Agents".

Smith, C., et. al., Bioorganic & Medicinal Chemistry Letters, 6(1), pp 47–50 "RP 73163: A Bioabailable Alkylsulfinyl–Diphenylimidazole ACAT Inhibitor".

Snow et. al., Journal of American Chemical Society, 116, pp 10860–10869 (1994) "Studies on Proline Bornic Acid Dipeptide Inhibitors of Dipeptidyl Peptidase IV: Identification of a Cyclic Species containing a B—N Bond[1]".

Stout et. al., Chemtracts: Org. Chem. (1995), 8(6), pp. 359–62, or TS–962 (Taisho Pharmaceutical Co. Ltd). "Inhibitors of Acyl–Co A: Cholesterol O–Acyl Transferese (ACAT) as Hypocholesterolemic Agents 6. The First Water Soluble ACAT Inhibitor with Lipid–Regulating Activity".

Truett et. al., Proc. Natl. Acad. Sci. USA vol. 88, pp. 7806–7809, Sep. 1991 The Zucker rat obesity gene fatty (fa) maps to chromosome 5: Evidence for homology with the mouse gene diabetes (db).

Tverezovsky et. al., Tetrahedron, 1997, 53, pp. 14773–14792 "Synthesis of (2S, 3R, 4S)–3–4–Methanoproline and analogues by Cyclopropylidene Insertion".

Villhauer et. al., J. Med Chem. 2003, 46, 2774–2789 "1-[[(3–Hydroxy–1–adamantyl)amino]acetyl]–2–cyano–(S)–pyrrolidine: A Potent, Selective, and Orally Bioavailable Dipeptidyl Peptidase IV Inhibitor with Antihyperglycemic Properties".

Wermuth et. al., (Academic Press, 1996) The Practice of Medicinal Chemistry Chapter 31 "Designing Prodrugs and Bioprecursors 1: Carrier Prodrugs".

Yamada et. al., Bioorganic & Medicinal Chemistry Letters 8 (1998) pp. 1537–1540 "A Potent Dipeptide Inhibitor of Dipeptidyl Peptidase IV".

* cited by examiner

ADAMANTYLGLYCINE-BASED INHIBITORS OF DIPEPTIDYL PEPTIDASE IV AND METHODS

This application claims priority to U.S. Provisional Application Ser. No. 60/491,832 filed Aug. 1, 2003. The entirety of this application is incorporated herein by reference.

FIELD OF THE INVENTION

The present invention relates to adamantylglycine-based inhibitors of dipeptidyl peptidase IV (DPP-4), to methods for employing such compounds alone or in combination with another type of therapeutic agent.

BACKGROUND OF THE INVENTION

Depeptidyl peptidase IV (DPP4) is a membrane bound non-classical serine aminodipeptidase which is located in a variety of tissues (intestine, liver, lung, kidney) as well as on circulating T-lymphocytes (where the enzyme is known as CD-26). DPP-4 is believed responsible for the metabolic cleavage of certain endogenous peptides (GLP-1(7-36), glucagon) in vivo and has demonstrated proteolytic activity against a variety of other peptides (GHRH, NPY, GLP-2, VIP) in vitro.

GLP-1(7-36) is a 29 amino-acid peptide derived by post-translational processing of proglucagon in the small intestine. GLP-1(7-36) has multiple actions in vivo including the stimulation of insulin secretion, inhibition of glucagon secretion, the promotion of satiety, and the slowing of gastric emptying. Based on its physiological profile, the actions of GLP-1(7-36) are expected to be beneficial in the prevention and treatment of type II diabetes and potentially obesity. To support this claim, exogenous administration of GLP-1(7-36) (continuous infusion) in diabetic patients has demonstrated efficacy in this patient population. Unfortunately GLP-1(7-36) is degraded rapidly in vivo and has been shown to have a short half-life in vivo (t½≈1.5 min). Based on a study of genetically bred DPP-4 KO mice and on in vivo/in vitro studies with selective DPP-4 inhibitors, DPP-4 has been shown to be the primary degrading enzyme of GLP-1(7-36) in vivo. GLP-1(7-36) is degraded by DPP-4 efficiently to GLP-1(9-36), which has been speculated to act as a physiological antagonist to GLP-1(7-36). Thus, inhibition of DPP-4 in vivo should potentiate endogenous levels of GLP-1(7-36) and attenuate formation of its antagonist GLP-1(9-36), thereby serving to ameliorate the diabetic condition.

DESCRIPTION OF THE INVENTION

In accordance with the present invention, compounds of formula (I) are provided

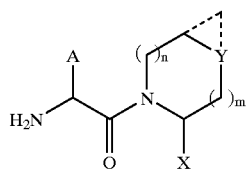

wherein:

n is 0, 1 or 2;

m is 0, 1 or 2;

the sum of n plus m is less then or equal to 2 the dashed bonds forming a cyclopropyl ring can only be present when Y is CH;

X is H or CN;

Y is CH, $CH_2$, CHF, $CF_2$, O, S, SO, or $SO_2$

A is adamantyl which can be optionally substituted with from zero to six substituents each independently selected from $OR^1$, $NR^1R^2$, alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, aralkyl, heteroaryl, heteroarylalkyl, cycloheteroalkyl and cycloheteroalkylalkyl, all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

$R^1$ and $R^2$ are each independently selected from hydrogen, alkyl, alkenyl, alkynyl, aryl and heteroaryl;

with the proviso that the compound of formula (I) is not selected from

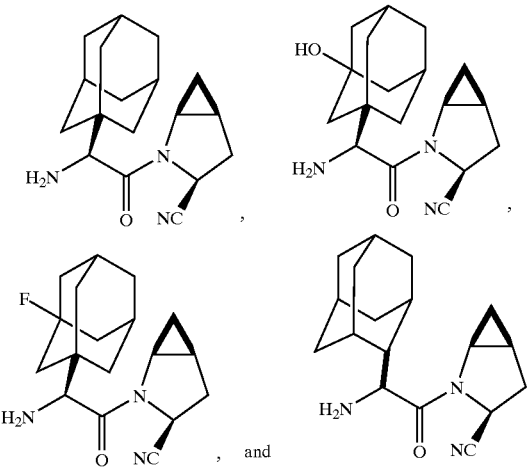

The definition of formula I above includes all pharmaceutically acceptable salts, stereoisomers, and prodrug esters of formula I.

The compounds of formula I possess activity as inhibitors of DPP-4 in vivo and are useful in the treatment of diabetes and the micro- and macrovascular complications of diabetes such as retinopathy, neuropathy, nephropathy, and wound healing. Such diseases and maladies are also sometimes referred to as "diabetic complications".

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further provided is a method for treating or delaying the progression or onset of diabetes, especially type II diabetes, including complications of diabetes, including retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis and hypertension, and for increasing high density lipoprotein levels, wherein a therapeutically effective amount of a compound of formula I is administered to a mammalian, e.g., human, patient in need of treatment.

The compounds of the invention can be used alone, in combination with other compounds of the present invention, or in combination with one or more other agent(s) active in the therapeutic areas described herein.

In addition, a method is provided for treating diabetes and related diseases as defined above and hereinafter, wherein a therapeutically effective amount of a combination of a compound of formula I and at least one other type of therapeutic agent, such as an antidiabetic agent and/or a hypolipidemic agent, is administered to a human patient in need of treatment.

Further embodiments of the present invention include compounds of formula (I) selected from

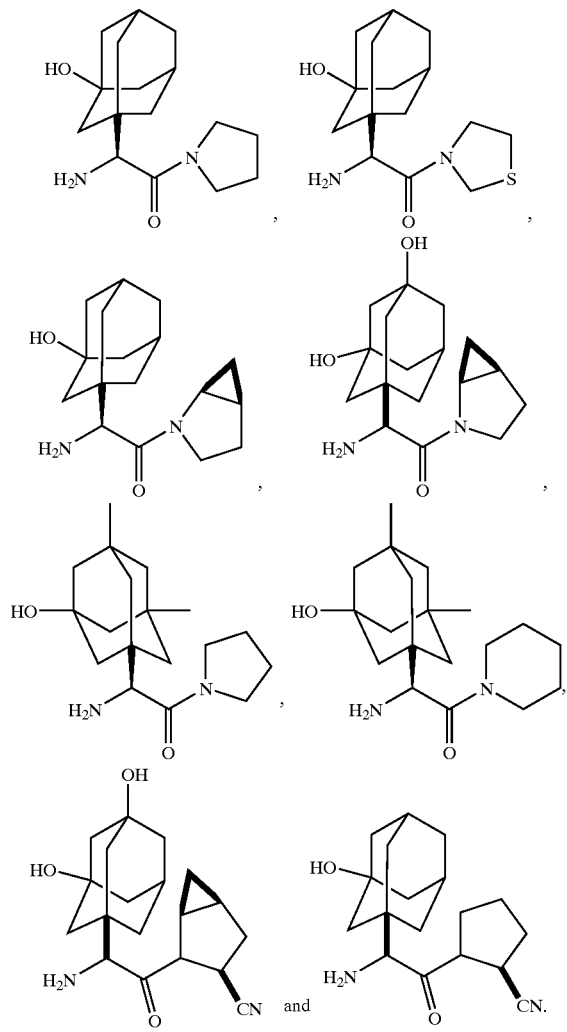

In the above method of the invention, the compound of formula (I) will be employed in a weight ratio to the antidiabetic agent or other type therapeutic agent (depending upon its mode of operation) within the range from about 0.01:1 to about 500:1, preferably from about 0.1:1 to about 100:1, more preferably from about 0.2:1 to about 10:1.

DETAILED DESCRIPTION OF THE INVENTION

The compounds of the present invention provide very potent DPP-IV inhibitory activity in vitro against the human enzyme, where Ki's were measured using natural and psuedosubstrates. Further, in rodent models of impaired glucose homeostasis, the claimed compounds provided more effective reduction in peak and 4 hour area under the curve (AUC) plasma glucose after an oral glucose challenge.

Inhibitors of serine proteases such as DPP-IV can often be characterized by their resemblance to the native substrates or portions thereof, cleaved by the specific enzyme. A standard nomenclature established by Schecter and Berger (I. Schecter, A. Berger, *Biochem. Biophys. Res. Commun.* 1967, 27, 157) denotes those residues of the substrate (or inhibitor) which bind in enzyme pockets on either side of the scissile peptidic bond as P1 and P1', with sequential numbering in the amino terminal direction following on as P2, P3 etc., and in the carboxy terminal direction as P2', P3' etc. As the enzyme DPP-IV cleaves the amino terminal (N-terminal) dipeptide from substrates with the appropriate recognition sequence, the N-terminus of DPP-IV substrates is generally synonymous with the P2 moiety. The present series of inhibitors of DPP-IV consists of compounds which bind to the same pockets occupied by the P2 and P1 residues of the native substrates, referred to as the S2 and S1 pockets in the enzyme. For example, the adamantylglycine pyrrolidide compound illustrated below contains a P2 unit and a P1 unit.

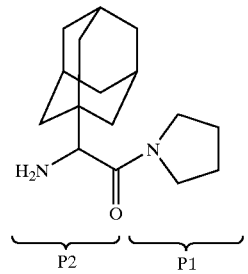

The compounds of the present invention all contain an adamantyl moiety or substituted adamantyl moiety in the P2 position, with varied P1 units. Our extensive investigations of various inhibitors of DPP-IV has revealed that in fixing the P2 unit as an adamantyl- or substituted adamantyl-containing glycine moiety, that a marked, measurable beneficial effect on in vitro DPP-IV inhibitory potency and/or enhanced activity in animal models of impaired glucose homeostasis has resulted. We have further observed that this effect is consistent across a broad range of P1 components, whereby within each respective subclass of inhibitors defined by the P1 moiety, that the presence of the adamantyl- or substituted adamantyl-glycine moiety in the P2 position confers activity to the whole inhibitor which is superior to those of the given subclass defined by the P1 moiety with non-adamantyl containing P2 units.

The compounds of formula I of the invention can be prepared as shown in the following reaction schemes and description thereof, as well as relevant published literature procedures that may be used by one skilled in the art. Exemplary reagents and procedures for these reactions appear hereinafter in the working Examples.

Scheme 1

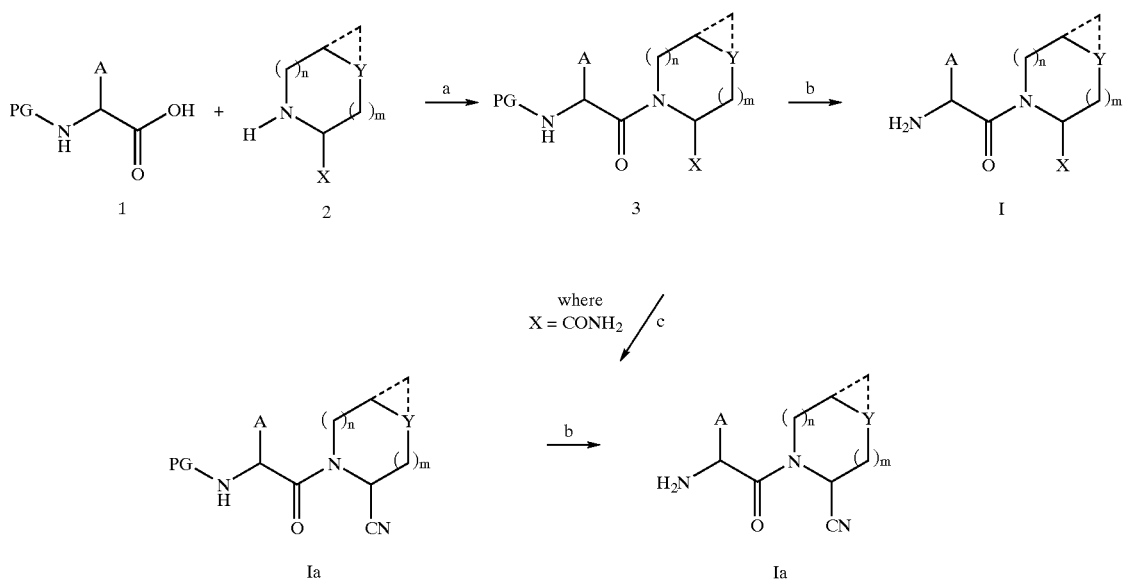

Reagents and conditions: a. EDAC, HOBT, DMF or i-BuOCOCl/TEA or PyBop, NMM b. PG=Boc, TFA or HCl; PG=Cbz, $H_2$/Pd/C or TMSI; PG=FMOC, $Et_2NH$. c. $POCl_3$, pyridine, imidazole or cyanuric chloride, DMF, or TFAA, pyridine.

Referring to Reaction Scheme 1, compound 1, where PG is a common amine protecting group such as Boc, Cbz, or FMOC as set out below, may be generated by methods as described herein or in the literature (for example, see Robi et. al., U.S. Pat. No. 6,395,767).

Referring to Reaction Scheme 1, compound 2 where X is H or $CONH_2$ may be obtained from commercial sources, or alternatively generated by methods as described herein or in the literature (for example, see Sagnard et. al., Tetrahedron Lett., 1995, 36, pp. 3148–3152; Tverezovsky et. al., Tetrahedron, 1997, 53, pp.14773–14792; Hanessian et. al., Bioorg. Med. Chem. Lett., 1998, 8, p. 2123–2128; Robl et. al., U.S. Pat. No. 6,395,767; Villhauer et. al., U.S. Pat. No. 6,110,949; Jenkins et. al., U.S. Pat. No. 5,939,560; Evans et. al., WO 01/81337; Broqua et. al., WO 02/083109; Pitt et. al., WO 03/000250; Ashton et. al., WO 02/076450; Haffner et. al., WO 03/002530, Haffner et. al., WO 03/002531). Amine 2 may be coupled to various protected substituted adamantylglycine amino acids (1) (where PG can be any of the PG protecting groups) using standard peptide coupling conditions (e.g. EDAC/HOAT, i-BuCOCOC1/TEA, PyBop/NMM) to afford the corresponding protected dipeptide 3. Where X=H, removal of the amine protecting group PG provides compound I of the invention. Where $X=CONH_2$, dehydration to a cyano (CN) group may be accomplished by, use of appropriate dehydrating conditions, such as for example TFAA/pyridine or $POCl_3$/pyridine/imidazole. Subsequent removal of the protecting group as previously described provides a compound of formula Ia.

Scheme 2

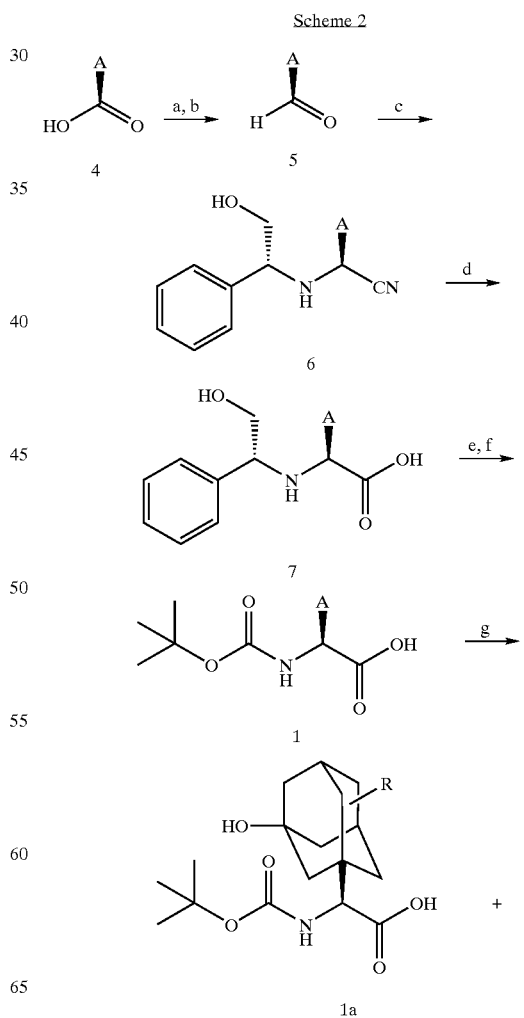

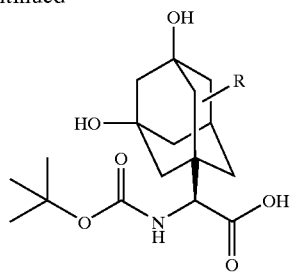

1b

Reagents and conditions: a. LAH, or esterification then LAH b. Swern Oxidation, or TEMPO, NaOCl c.R-(−)-2-Phenylglycinol, NaHSO3, KCN d. 12M HCl, HOAc, 80 C, 16h, 78% d. 12M HCl, HOAC, 80 C, 16h, 78% e. 20% Pd(OH)2, 50 psi H2, MeOH:HOAc, 5:1 f. (Boc)2O, K2CO3, DMF, 92%, 2 steps. g. KMnO4, Heat, KOH 30–90%.

Scheme 2 provides a general route to protected, substituted adamantylglycine amino acids (1) by an asymmetric Strecker Reaction. Carboxylic acids 4 can be esterified using for example either MeOH with HCl at reflux or using trimethylsilyldiazomethane in $Et_2O$/methanol to give methyl esters. Reduction of the ester group with LAH to the alcohol and subsequent oxidation (for example Swern oxidation) gives aldehydes 5. Aldehyde 5 can be transformed to 6 under asymmetric Strecker conditions with KCN, $NaHSO_3$ and R-(−)-2-phenylglycinol. The nitrile group of 6 can then be hydrolyzed under strongly acidic conditions, using, for example, 12M HCl in HOAc to give the carboxylic acids 7. The chiral auxiliary can then be removed by catalytic reduction using, for example, Pearlman's catalyst in acidic methanol under 50 psi hydrogen to give, after protection of the resulting amino group, as for example the t-butylcarbamate, protected adamantylglycine amino acids 1. Further elaboration of the functionality of protected adamantylglycine amino acids 1 can be carried out prior to coupling with amines 2, such as oxidation to hydroxyadamantyl compounds 1a or 1b, with a suitable oxidizing agent, such as for example, $KMnO_4$.

Scheme 3

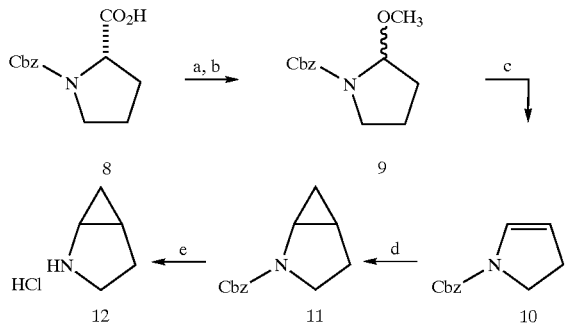

Reagents and conditions: (a) iodobenzene diacetate, $I_2$, $CH_2Cl_2$, rt; (b) MeOH, rt; (c) TMSOTf, N,N-diisopropylethylamine, $CH_2Cl_2$, 0° C.; (d) diethylzinc, $ClCH_2I$, $Et_2O$, 0° C. to rt; (e) $H_2$, 10% Pd/C, HCl, EtOH.

For certain amine moieties (2), synthetic sequences are outlined herein in Schemes 3 and 4. For example, the racemic synthesis of 2,3-methanopyrrolidine is outlined in Scheme 3. Commercially available Cbz-protected L-proline (8) was oxidatively decarboxylated by treatment with iodobenzene diacetate and elemental iodine in dichloromethane, followed by stirring in methanol to provide the racemic protected 2-methoxypyrrolidine 9. Dehydration of methoxy compound 9 was achieved by treatment with Hunig's base and trimethylsilyl triflate to give protected dihydropyrrole 10. Standard cyclopropanation conditions (diethylzinc, chloroiodomethane) to give the methano product 11, followed by deprotection of the benzyloxycarbonyl (Cbz) group under acidic conditions afforded the racemic 2,3-methanopyrrolidine as the corresponding hydrochloride salt.

Scheme 4

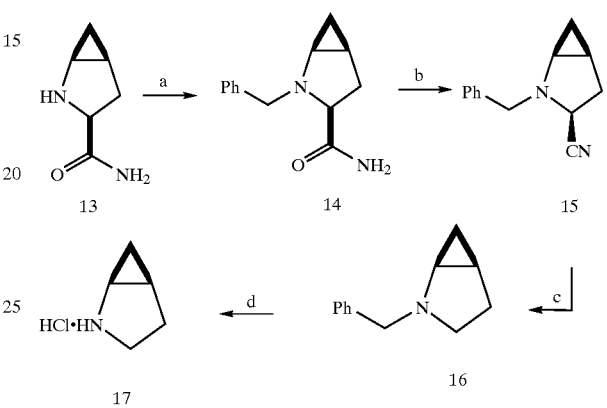

Reagents and conditions: (a) benzyl bromide, N,N-diisopropylethylamine, $CH_2Cl_2$, rt; (b) trifluoroacetic acid anhydride, TEA, $CH_2Cl_2$, 0° C.; (c) $NaBH_4$, $EtOH/H_2O$, rt; (d) 1-chloroethyl chloroformate, $CH_2Cl_2$, reflux.

A route to the homochiral methanopyrrolidine is outlined in Scheme 4. Beginning with (L)-cis-4,5-methanoprolinamide 13 (see Robi et. al. U.S. Pat. No. 6,395,767), protection of the proline nitrogen can be accomplished using benzyl bromide and Hunig's base in dichloromethane to give intermediate 14. Dehydration of the amide to the corresponding nitrile can be achieved using trifluoroacetic anhydride and triethylamine in dichloromethane to give cyano compound 15. Reductive removal of the cyano group of 15 by treatment with, for example sodium borohydride in aqueous ethanol affords benzyl protected methanopyrrolidine 16. Removal of the benzyl protecting group can be accomplished by treatment with α-chloroethyl acetyl chloride (ACE-Cl) in refluxing dichloromethane to give the desired (2S,3R)-2,3-methanopyrrolidine 17 in optically pure form as the hydrochloride salt.

The following definitions apply to the terms as used throughout this specification, unless otherwise limited in specific instances.

The term adamantyl as employed herein alone or as part of another group refers to:

Optionally, said adamantyl group may be substituted with one or more substitutants as those defined for alkyl and as defined in the claims and detailed description herein.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof. Optionally, said alkyl groups may be substituted with one or more substitutants, such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

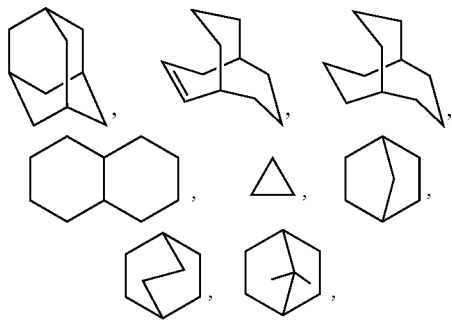

any of which groups may be optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

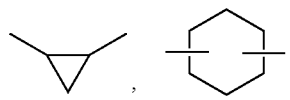

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl,-cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

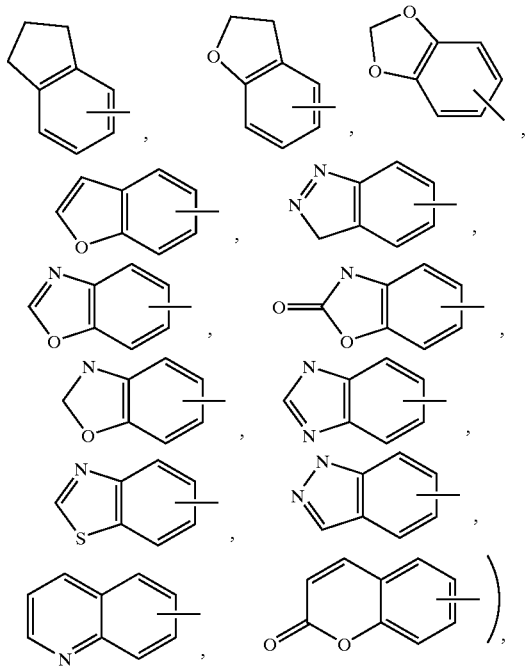

, and may be optionally substituted through available carbon atoms with one or more groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfon-aminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the R$^1$ groups or substituents for R$^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the R$^1$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker (CH$_2$)$_r$ (where r is 1, 2 or 3), such as:

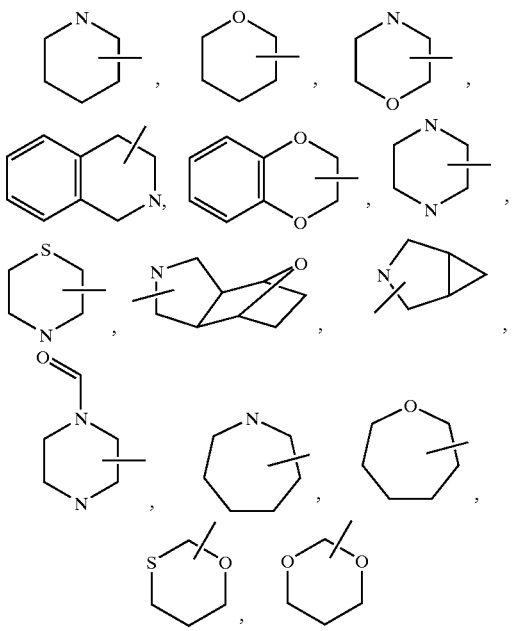

and the like. The above groups may include 1 to 4 substituents such as alkyl, halo, oxo and/or any of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include one or more substituents such as any of the substituents set out above for alkyl. Examples of heteroaryl groups include the following:

and the like.

The term "cycloheteroalkylalkyl" as used herein alone or as part of another group refers to cycloheteroalkyl groups as defined above linked through a C atom or heteroatom to a $(CH_2)_r$ chain.

The term "heteroarylalkyl" or "heteroarylalkenyl" as used herein alone or as part of another group refers to a heteroaryl group as defined above linked through a C atom or heteroatom to a $—(CH_2)_r—$ chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkoxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "thiol" or "thio" as used herein, refers to (—S)or (—S—).

The term "alkylthio" refers to an alkyl group linked to the parent molecular moiety through a thiol group.

The term "alkylthioalkyl" refers to an alkylthio group linked to the parent molecular moiety through an alkyl group.

The term "arylalkylthioalkyl" refers to Ar-alkyl-S-alkyl-.

The term "alkoxycarbonyl," as used herein, refers to an alkoxy group, as defined herein, appended to the parent molecular moiety through a carbonyl group, as defined herein.

The term "cyano," as used herein, refers to a —CN group.
The term "carboxyl" denotes —C(O)O—.
The term "nitro" as used herein, refers to a —$NO_2$ group.
The term "sulfonyl" as used herein, refers to an $SO_2$ group
The term "sulfinyl" as used herein, refers to an SO group The term "hydroxyalkyl" as used herein, refers to an "alkyl" or "cycloalkyl" group as defined above which preferably includes from 1 to 3 hydroxy substituents The term "aminocarbonyl" refer to an amino group, herein a $NR^5R^{5'}$ group, linked through a carbonyl group, as defined herein, to the parent molecular moiety.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

The conditions, diseases and maladies collectively referred to as "diabetic complications" include retinopathy, neuropathy and nephropathy, erectile dysfunction, and other known complications of diabetes.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a.) *The Practice of Medicinal Chemistry*, Camille G. Wermuth et al., Ch 31, (Academic Press, 1996);

b.) *Design of Prodrugs*, edited by H. Bundgaard, (Elsevier, 1985); and c.) *A Textbook of Drug Design and Development*, P. Krogsgaard-Larson and H. Bundgaard, eds. Ch 5, pgs 113–191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The term "other type of therapeutic agents" as employed herein includes, but is not limited to one or more antidiabetic agents (other than DPP-IV inhibitors of formula I), one or more anti-obesity agents, one or more anti-hypertensive agents, one or more anti-platelet agents, one or more anti-atherosclerotic agents and/or one or more lipid-lowering agents (including anti-atherosclerosis agents).

UTILITY & COMBINATIONS

A. Utilities

The compounds of the present invention possess activity as inhibitors of the dipeptidyl peptidase IV which is found in a variety of tissues, such as the intestine, liver, lung and kidney of mammals. Via the inhibition of dipeptidyl peptidase IV in vivo, the compounds of the present invention possess the ability to potentiate endogenous levels of GLP-1(7-36) and attenuate formation of its antagonist GLP-1(9-36).

In particular, the compounds of the present invention provide very potent DPP-IV inhibitory activity in vitro against the human enzyme, where Ki's were measured using natural and psuedosubstrates. Further, in rodent models of impaired glucose homeostasis, the claimed compounds provided more effective reduction in peak and 4 hour area under the curve (AUC) plasma glucose after an oral glucose challenge.

Accordingly, the compounds of the present invention can be administered to mammals, preferably humans, for the treatment of a variety of conditions and disorders, including, but not limited to, treating or delaying the progression or onset of diabetes(preferably Type II, impaired glucose tolerance, insulin resistance, and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis and hypertension. The compounds of the present invention may also be utilized to increase the blood levels of high density lipoprotein (HDL).

In addition, the conditions, diseases, and maladies collectively referenced to as "Syndrome X" or Metabolic Syndrome as detailed in Johannsson *J. Clin. Endocrinol. Metab.*, 82, 727–34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may employed in combination with other inhibitors of DPP-4 activity or other suitable therapeutic agents useful in the treatment of the aforementioned disorders including: anti-diabetic agents; anti-hyperglycemic agents; hypolipidemic/lipid lowering agents; anti-obesity agents; anti-hypertensive agents and appetite supressants.

Examples of suitable anti-diabetic agents for use in combination with the compounds of the present invention include biguanides (e.g., metformin or phenformin), glucosidase inhibitors (e.g,. acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1), and SGLT2 inhibitors.

It is believed that the use of the compounds of formula I in combination with at least one or more other antidiabetic agent(s) provides antihyperglycemic results greater than that possible from each of these medicaments alone and greater than the combined additive anti-hyperglycemic effects produced by these medicaments.

Other suitable thiazolidinediones include Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. Pat. No. 6,414,002, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Other suitable DPP4 inhibitors that may be used in combination with the compounds of the invention include those disclosed in WO99/38501, WO99/46272, WO99/67279 (PROBIODRUG), WO99/67278 (PROBIODRUG), WO99/61431 (PROBIODRUG), U.S. Pat. No. 6,935,767, MRK-0431, Nevaglitizar (Lilly & Ligand), LAF-237 (Novartis) as disclosed in E. B Villhauer et. al., J. Med Chem. 2003, 46, 2774–2789, and B. Ahren et. al., J. Clin. Endocrin. & Metab. 2004, 89 (5), 2078–2084. TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides, as disclosed by Ashworth et al, Bioorg. & Med. Chem. Lett., Vol. 6, No. 22, pp 1163–1166 and 2745–2748 (1996) employing dosages as set out in the above references.

Suitable meglitinides include nateglinide (Novartis) or KAD1229 (PF/Kissei).

Examples of suitable anti-hyperglycemic agents for use in combination with the compounds of the present invention include glucagon-like peptide-I (GLP-I,) such as GLP-I(I-36) amide, GLP-I(7-36) amide, GLP-I(7-37) (as disclosed in U.S. Pat. No. 5,614,492 to Habener), as well as Exendin4 (AC2993-Amylin) and LY-315902 (Lilly).

Examples of suitable hypolipidemic/lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., CP-529414 (Pfizer)) and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983 and 5,962,440.

The HMG CoA reductase inhibitors which may be employed in combination with one or more compounds of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681, 893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753, 675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl) pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596, 393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No.0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates, as well as other known squalene synthetase inhibitors, for example, as disclosed in U.S. Pat. No. 4,871, 721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98,1291–1293, phosphinylphosphonates reported by McClard, R. W. et al, J. A. C. S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

The fibric acid derivatives which may be employed in combination with one or more compounds of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives, such as disclosed in U.S. Pat. No. 4,759,923, quaternary amine poly (diallyidimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future 24, 9–15 (1999), (Avasimibe); "The ACAT inhibitor, CI-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitor for use in combination with the compounds of the invention include SCH48461 (Schering-Plough), as well as those disclosed in Atherosclerosis 115, 45–63 (1995) and J. Med. Chem. 41, 973 (1998).

Examples of suitable ileal $Na^+$/bile acid cotransporter inhibitors for use in combination with the compounds of the invention include compounds as disclosed in Drugs of the Future, 24, 425–430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/All antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a beta 3 adrenergic agonist, a lipase inhibitor, a serotonin (and dopamine) reuptake inhibitor, a thyroid receptor beta drug and/or an anorectic agent.

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770, 615, 5,491,134, 5,776,983 and 5,488,064, with AJ9677, L750,355 and CP331648 being preferred.

Examples of lipase inhibitors which may be optionally employed in combination with compounds of the present invention include orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

Examples of thyroid receptor beta compounds which may be optionally employed in combination with compounds of the present invention include thyroid receptor ligands, such as those disclosed in WO97/21993 (U. Cal SF), WO99/00353 (KaroBio) and GB98/284425 (KaroBio), with compounds of the KaroBio applications being preferred.

The anorectic agent which may be optionally employed in combination with compounds of the present invention include dexamphetamine, phentermine, phenylpropanolamine or mazindol, with dexamphetamine being preferred.

The aforementioned patents and patent applications are incorporated herein by reference.

The above other therapeutic agents, when employed in combination with the compounds of the present invention may be used, for example, in those amounts indicated in the Physician's Desk Reference, as in the patents set out above or as otherwise determined by one of ordinary skill in the art.

Where the compounds of the invention are utilized in combination with one or more other therapeutic agent(s), either concurrently or sequentially, the following combination ratios and dosage ranges are preferred. Where the other antidiabetic agent is a biguanide, the compounds of formula I will be employed in a weight ratio to biguanide within the range from about 0.01:1 to about 100:1, preferably from about 0.1:1 to about 5:1.

The compounds of formula I will be employed in a weight ratio to the glucosidase inhibitor within the range from about 0.01:1 to about 100:1, preferably from about 0.5:1 to about 50:1.

The compounds of formula I will be employed in a weight ratio to the sulfonyl urea in the range from about 0.01:1 to about 100:1, preferably from about 0.2:1 to about 10:1.

The compounds of formula I will be employed in a weight ratio to the thiazolidinedione in an amount within the range from about 0.01:1 to about 100:1, preferably from about 0.2:1 to about 10:1.

Where present, the thiazolidinedione anti-diabetic agent may be employed in amounts within the range from about 0.01 to about 2000 mg/day which may be administered in single or divided doses one to four times per day.

Optionally, the sulfonyl urea and thiazolidinedione may be incorporated in a single tablet with the compounds of formula I in amounts of less than about 150 mg.

Where present, metformin or salt thereof may be employed in amounts within the range from about 500 to about 2000 mg per day which may be administered in single or divided doses one to four times daily.

Where present GLP-I peptides may be administered in oral buccal formulations, by nasal administration or parenterally as described in U.S. Pat. Nos. 5,346,701 (TheraTech), 5,614,492 and 5,631,224 which are incorporated herein by reference.

The DPP-IV inhibitor of formula I will be employed in a weight ratio to the meglitinide, PPAR-gamma agonist, PPAR-alpha/gamma dual agonist, aP2 inhibitor or SGLT2 inhibitor within the range from about 0.01:1 to about 100:1, preferably from about 0.2:1 to about 10:1.

The compounds of formula I of the invention will be generally be employed in a weight ratio to the hypolipidemic agent (were present), within the range from about 500:1 to about 1:500, preferably from about 100:1 to about 1:100.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor in an amount within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

The squalene synthetase inhibitor may be employed in dosages in an amount within the range of from about 10 mg to about 2000 mg and preferably from about 25 mg to about 200 mg.

A preferred oral dosage form, such as tablets or capsules will contain the squalene synthetase inhibitor in an amount of from about 10 to about 500 mg, preferably from about 25 to about 200 mg.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out a preferred method of the invention for treating any of the diseases disclosed herein, such as diabetes and related diseases, a pharmaceutical composition will be employed containing one or more of the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 10 to about 500 mg of a compound of formula I. The dose for adults is preferably between 10 and 2,000 mg per day, which can be administered in a single dose or in the form of individual doses from 1–4 times per day.

A typical injectable preparation may be produced by aseptically placing 250 mg of compounds of formula I into a vial, aseptically freeze-drying and sealing. For use, the contents of the vial are mixed with 2 mL of physiological saline, to produce an injectable preparation.

A typical capsule for oral administration contains compounds of structure I (250 mg), lactose (75 mg) and magnesium stearate (15 mg). The mixture is passed through a 60 mesh sieve and packed into a No. 1 gelatin capsule.

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

DPP-4 inhibitor activity of the compounds of the invention may be determined by use of an in vitro assay system which measures the potentiation of inhibition of DPP-4. Inhibition constants (Ki values) for the DPP-4 inhibitors of the invention may be determined by the method described the experimental section.

Purification of Porcine Dipeptidyl Peptidase IV

Porcine enzyme was purified as previously described in reference (2) below, with several modifications. Kidneys from 15–20 animals were obtained, and the cortex was dissected away and frozen at −80° C. Frozen tissue (2000–2500 g) was homogenized in 12 L of 0.25 M sucrose in a Waring blender. The homogenate then was left at 37° C. for 18 hours to facilitate cleavage of DPP-4 from cell membranes. After the cleavage step, the homogenate was clarified by centrifugation at 7000×g for 20 min at 4° C., and the supernatant was collected. Solid ammonium sulfate was added to 60% saturation, and the precipitate was collected by centrifugation at 10,000×g and was discarded. Additional ammonium sulfate was added to the supernatant to 80% saturation, and the 80% pellet was collected and dissolved in 20 mM $Na_2HPO_4$, pH 7.4.

After dialysis against 20 mM $Na_2HPO_4$, pH 7.4, the preparation was clarified by centrifugation at 10,000×g. The clarified preparation then was applied to 300 mL of ConA Sepharose that had been equilibrated in the same buffer. After washing with buffer to a constant $A_{280}$, the column was eluted with 5% (w/v) methyl α-D-mannopyranoside. Active fractions were pooled, concentrated, and dialyzed against 5 mM sodium acetate, pH 5.0. Dialyzed material then was flowed through a 100 mL Pharmacia Resource S column equilibrated in the same buffer. The flow through material was collected and contained most of the enzyme activity. Active material again was concentrated and dialyzed into 20 mM $Na_2HPO_4$, pH 7.4. Lastly, the concentrated enzyme was chromatographed on a Pharmacia S-200 gel filtration column to removed low molecular weight contaminants. Purity of column fractions was analyzed by reducing SDS-PAGE, and the purest fractions were pooled and concentrated. Purified enzyme was stored in 20% glycerol at −80° C.

Assay of Porcine Dipeptidyl Peptidase IV

Enzyme was assayed under steady-state conditions as previously described in reference (2) below with gly-pro-p-nitroanilide as substrate, with the following modifications. Reactions contained, in a final volume of 100 $\mu$l, 100 mM Aces, 52 mM TRIS, 52 mM ethanolamine, 500 $\mu$M gly-pro-p-nitroanilide, 0.2% DMSO, and 4.5 nM enzyme at 25° C., pH 7.4. For single assays at 10 $\mu$M test compound, buffer, compound, and enzyme were added to wells of a 96 well microtiter plate, and were incubated at rt for 5 min. Reactions were started by addition of substrate. The continuous production of p-nitroaniline was measured at 405 nM for 15 min using a Molecular Devices Tmax plate reader, with a read every 9 seconds. The linear rate of p-nitroaniline production was obtained over the linear portion of each progress curve. A standard curve for p-nitroaniline absorbance was obtained at the beginning of each experiment, and enzyme catalyzed p-nitroaniline production was quantitated from the standard curve. Compounds giving greater than 50% inhibition were selected for further analysis.

For analysis of positive compounds, steady-state kinetic inhibition constants were determined as a function of both substrate and inhibitor concentration. Substrate saturation curves were obtained at gly-pro-p-nitroanilide concentrations from 60 $\mu$M to 3600 $\mu$M. Additional saturation curves also were obtained in the presence of inhibitor. Complete inhibition experiments contained 11 substrate and 7 inhibitor concentrations, with triplicate determinations across plates. For tight binding inhibitors with $K_i$s less than 20 nM, the enzyme concentration was reduced to 0.5 nM and reaction times were increased to 120 min. Pooled datasets from the three plates were fitted to the appropriate equation for either competitive, noncompetitive or uncompetitive inhibition.

(1) Rahfeld, J. Schutkowski, M., Faust, J., Neubert., Barth, A., and Heins, J. (1991) Biol. Chem. Hoppe-Seyler, 372, 313–318.

(2) Nagatsu, T., Hino, M., Fuyamada, H., Hayakawa, T., Sakakibara, S., Nakagawa, Y., and Takemoto, T. (1976) Anal. Biochem., 74, 466–476.

The following abbreviations are employed in the Examples and elsewhere herein:

Ph = phenyl
Bn = benzyl
i-Bu = iso-butyl
Me = methyl
Et = ethyl
Pr = propyl
Bu = butyl
TMS = trimethylsilyl
FMOC = fluorenylmethoxycarbonyl
Boc or BOC = tert-butoxycarbonyl
HOAc or AcOH = acetic acid
DMF = N,N-dimethylformamide
DMSO = dimethylsulfoxide
EtOAc = ethyl acetate
THF = tetrahydrofuran
TFA = trifluoroacetic acid
Et$_2$NH =diethylamine
NMM = N-methyl morpholine
n-BuLi = n-butyllithium
Pd/C = palladium on carbon
PtO$_2$ = platinum oxide
TEA = triethylamine
equiv = equivalent(s)
min = minute(s)
h or hr = hour(s)
L = liter
mL = milliliter
µL = microliter
g = gram(s)
mg = milligram(s)
mol = mole(s)
mmol = millimole(s)
meq = milliequivalent
rt = room temperature
sat or sat'd = saturated
aq. = aqueous
TLC = thin layer chromatography
MS or Mass Spec = mass spectrometry
NMR = nuclear magnetic resonance
mp = melting point Cbz=carbobenzyloxy or carbobenzoxy or benzyloxycarbonyl
HPLC=high performance liquid chromatography
HPLC=high performance liquid chromatography/mass spectrometry
EDAC=3-ethyl-3'-(dimethylamino)propyl-carbodiimide hydrochloride (or 1-[(3-(dimethyl)amino)propyl])-3-ethylcarbodiimide hydrochloride)
HOBT or HOBT•H$_2$O=1-hydroxybenzotriazole hydrate
HOAT=1-hydroxy-7-azabenzotriazole
PyBOP reagent=benzotriazol-1-yloxy-tripyrrolidino phosphonium hexafluorophosphate The following examples are provided to describe the invention in further detail. These examples, which set forth the best mode presently contemplated for carrying out the invention, are intended to illustrate and not to limit the invention.

EXAMPLE 1

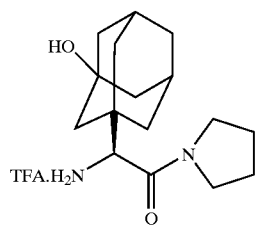

EXAMPLE 1

Step 1

Adamantane-1-carboxylic acid (10.0 g, 55 mmol, 1 equiv) was dissolved in a mixture of Et$_2$O (160 mL) and MeOH (40 mL), and was treated with trimethylsilyl diazomethane (2.0 M in hexane, 30 mL, 60 mmol, 1.1 equiv) and stirred at rt for 3 h. The volatiles were then removed by rotary evaporation and the product purified by flash column chromatography on silica gel (5×15 cm) with 40% CH$_2$Cl$_2$/hexanes to give the product as a white crystalline solid (10.7 g, 100%).

EXAMPLE 1

Step 2

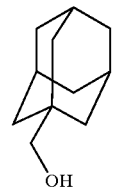

Step 1 compound (10.7 g, 0.055 mmol, 1 equiv) was dissolved in anhydrous THF (150 mL) under argon and was treated with a solution of LiAlH$_4$ (1 M in THF, 69 mL, 69 mmol, 1.25 equiv). After stirring at rt for 1.5 h, the reaction was cooled to 0° C. and quenched sequentially with H$_2$O (5.1 mL), 15% aq NaOH (5.1 mL), and H$_2$O (10.2 mL). After stirring at rt for 15 min, the slurry was vacuum filtered, and the solids washed with EtOAc (2×100 mL). The filtrate was concentrated by rotary evaporation and the resulting solid purified by flash column chromatography on silica gel (5×15 cm) with 10% EtOAc/CH$_2$Cl$_2$. This afforded the Step 2 product as a white solid (8.74 g, 96%).

EXAMPLE 1

Step 3

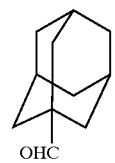

An oven-dried 3-neck flask equipped with 125-mL addition funnel was charged with anhydrous CH$_2$Cl$_2$ (150 mL) and anhydrous DMSO (10.3 mL, 0.145 mol, 2.5 equiv) under argon atmosphere and cooled to −78° C. Slow dropwise addition of oxalyl chloride (6.7 mL, 0.0768 mol, 1.32 equiv) followed by stirring for 15 min provided an activated DMSO adduct. This was treated with a solution of Step 2 compound (9.67 g, 58.2 mmol, 1 equiv) in dry CH$_2$Cl$_2$ (75 mL) and the reaction allowed to stir for 1 h. The resulting white mixture was then treated dropwise mixture was diluted with Et$_2$O (400 mL)and the layers were separated. The organics were washed organic with cold 10% aq KH$_2$PO$_4$ (3×150 mL) and satd aq NaCl (100 mL). The organics were dried (Na$_2$SO$_4$), filtered and concentrated. The residue was purified by flash column chromatography on silica gel (5×10 cm) with CH$_2$Cl$_2$ to give the Step 3 compound as a white solid (9.40 g, 98%).

EXAMPLE 1
Step 4

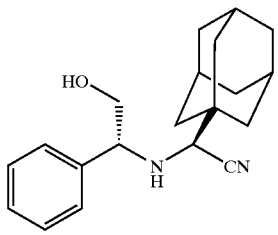

Step 3 compound (9.40 g, 57 mmol, 1 equiv) was suspended in H₂O (145 mL) and cooled to 0° C. The mixture was treated with NaHSO₃ (5.95 g, 57 mmol, 1 equiv), KCN (4.0 g, 59 mmol, 1.04 equiv), and a solution of (R)-(−)-phenylglycinol (8.01 g, 57 mmol, 1 equiv) in MeOH (55 mL). The resulting mixture was stirred at rt for 2 h, then refluxed for 16 h. The mixture was cooled to rt, and 200 mL of EtOAc added. After mixing for 15 min the layers were separated. The aqueous fraction was extracted with EtOAc. The combined EtOAc extracts were washed with brine (50 mL), dried over anhydrous Na₂SO₄, filtered and the filtrate concentrated. The product was purified by flash column chromatography on silica gel (6.4×20 cm) with 20% EtOAc/hexanes to give the desired (R,S) product as a white solid (11.6 g, 37.4 mmol, 65%): MS m/e 311 (M+H)⁺.

EXAMPLE 1
Step 5

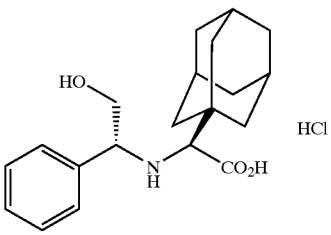

The Step 4 nitrile (5.65 g, 18 mmol) was heated in conc. HCl (120 mL) and HOAc (30 mL) at 80° C. for 18 h, at which time the reaction was cooled in an ice bath. Vacuum filtration of the resulting precipitate afforded the desired product as a white solid (5.21 g, 14 mmol, 78%). MS m/e 330 (m+H)⁺.

EXAMPLE 1
Step 6

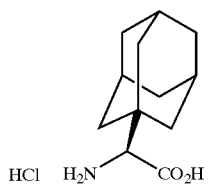

The Step 6 compound (5.21 g, 14 mmol) was dissolved in MeOH (50 mL) and HOAc (10 mL), and hydrogenated with H₂ (50 psi) and Pearlman's catalyst (20% Pd(OH)₂, 1.04 g, 20% w/w) for 18 h. The reaction was filtered through a PTFE membrane filter and the catalyst washed with MeOH (3×25 mL). The filtrate was concentrated by rotary evaporation to afford a white solid. The product was used in Step 7 without further purification.

EXAMPLE 1
Step 7

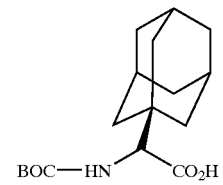

The crude Step 6 compound (@ 14 mmol) was dissolved in anhydrous DMF (50 mL) under argon and treated with K₂CO₃ (5.90 g, 42 mmol, 3 equiv) and di-tert-butyldicarbonate (3.14 g, 14 mmol, 1 equiv) under argon at rt. After 19 h, the DMF was removed by rotary evaporation (pump) and the residue dried further under reduced pressure. The residue was mixed with H₂O (100 mL) and Et₂O (100 mL), the layers separated, and the alkaline aqueous with Et₂O (2×100 mL) to remove the by-product from the hydrogenolysis step. The aqueous was cooled to 0° C., diluted with EtOAc (200 mL), and stirred vigorously while carefully acidifying the aqueous to pH 3 with 1N aq HCl. The layers separated and the aqueous extracted with EtOAc (100 mL). The combined EtOAc extracts were washed with brine (50 mL), dried (Na₂SO₄), filtered and the filtrate concentrated by rotary evaporation. The residue was purified by SiO₂ flash column (5×12 cm) with 5% MeOH/CH₂Cl₂+ 0.5% HOAc. The product was chased with hexanes to afford the product as a white foam (4.07 g, 13 mmol, 92%): MS m/e 310 (m+H)⁺.

EXAMPLE 1
Step 8

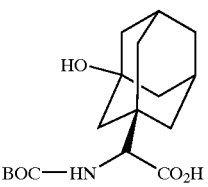

A solution of KMnO₄ (337 mg, 2.13 mmol, 1.1 equiv) in 2% aq KOH (6 mL) was heated to 60° C. and Step 7 compound in general method G (600 mg, 1.94 mmol, 1 equiv) was added in portions, and heating increased to 90° C. After 1.5 h, the reaction was cooled to 0° C., EtOAc (50 mL) was added, and the mixture was carefully acidified to pH 3 with 1N HCl. The layers were separated and the aqueous was extracted with EtOAc (50 mL). The combined organic extracts were washed with brine, dried over Na₂SO₄, filtered and concentrated. The residue was purified by flash column chromatography on silica gel (3.8×15 cm) with 2% (200 mL), 3% (200 mL), 4% (200 mL), and 5% (500 mL) MeOH/CH₂Cl₂+0.5% HOAc. After isolation of the product, the material was chased with hexanes to afford a white solid (324 mg, 51%): MS m/e 326 (m+H)⁺.

EXAMPLE 1

Step 9. (S)-[1-(3-Hydroxyadamantan-1-yl)-2-oxo-2-pyrrolidin-1-ylethyl]-carbamic acid tert-butyl ester

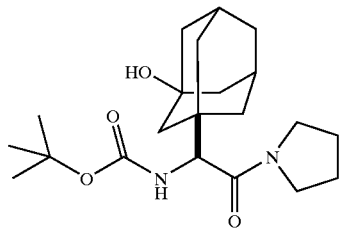

A solution of (S)-N-tert-butoxycarbonyl-2-hydroxyadamantylglycine (31.8 mg, 0.16 mmol, 1.0 equiv) and HOBT•H$_2$O (25 mg, 0.16 mmol, 1.0 equiv) in anhydrous CH$_2$Cl$_2$ was cooled to 0° C. and stirred for 30 min. The reaction mixture was treated sequentially with pyrrolidine (11.4 mg, 0.16 mmol, 1.0 equiv), EDAC (31 mg, 0.16 mmol, 1.0 equiv) and TEA (60 µL, 0.48 mmol, 3.0 equiv) and stirring continued at 0° C. for 30 min then at rt for 2 days. The mixture was partitioned between H$_2$O (1.5 mL) and EtOAc (2×20 mL) and the combined organic extracts were washed with brine (1.5 mL), dried (Na$_2$SO$_4$), filtered and concentrated. The product was purified by flash column chromatography on silica gel (2.2×8 cm) with an EtOAc/hexane gradient (0%-100%) to give Step 1 compound as a white foam (51.7 mg, 85.2%): MS m/e 380 (m+H)$^+$.

EXAMPLE 1

Step 10. (S)-[1-(3-Hydroxyadamantan-1-yl)-2-oxo-2-pyrrolidin-1-ylethyl]amine, trifluoroacetic acid salt.

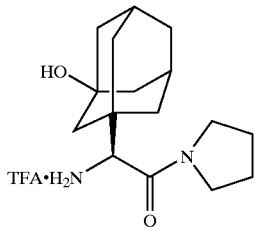

The Step 9 compound (48.2 mg, 0.13 mmol) was dissolved in TFA/CH$_2$Cl$_2$ (1:1, v/v, 0.44 mL) and stirred at rt. After 1.0 h, the solvents were removed by rotary evaporation, the remainder chased with toluene (2×4 mL) and Et$_2$O (2×20 mL). Trituration of the product with Et$_2$O followed by preparative HPLC afforded the title compound as a white solid (34.9 mg, 68.4%): MS m/e 279 (m+H)$^+$.

EXAMPLE 2

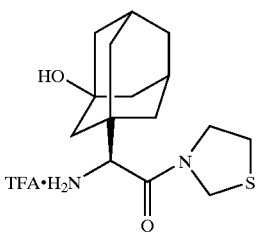

EXAMPLE 2

Step 1. (S)-[1-(3-Hydroxyadamantan-1-yl)-2-oxo-2-thiazolidin-3-ylethyl]-carbamic acid tert-butyl ester

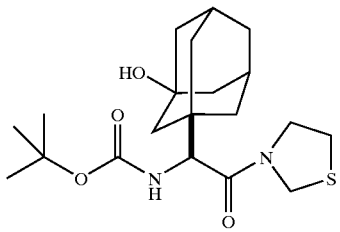

A solution of Example 1; step 8 compound, (S)-N-tert-butoxycarbonyl-2-hydroxyadamantyl glycine (70 mg, 0.215 mmol, 1.0 equiv) in dry DMF (2.1 mL) was cooled to 0° C. then treated sequentially with thiazolidine (20 µL, 0.237 mmol, 1.1 equiv), EDAC (88.2 mg, 0.46 mmol, 2.1 equiv), HOBT•H$_2$O (90.4 mg, 0.67 mmol, 3.1 equiv) and TEA (63 µL, 0.45 mmol, 2.1 equiv). Stirring was continued for 22 h, allowing the bath to come up to rt. The solvent was removed by rotary evaporation and the syrup obtained partitioned between EtOAc (2×70 mL) and saturated NaHCO$_3$ (14 mL). The combined organic extracts were washed with brine (10 mL), dried (Na$_2$SO$_4$), filtered and concentrated by rotary evaporation. The product was purified by flash chromatography on silica gel (2.5×14 cm) with CH$_2$Cl$_2$/CH$_3$OH (500 mL of 95:5) to afford the product as a solid white foam (81.6 mg, 95.7%): MS m/e 397 (m+H)$^+$.

EXAMPLE 2

Step 2. (S)-[1-(3-Hydroxyadamantan-1-yl)-2-oxo-2-thiazolidin-3-ylethyl]amine, trifluoroacetic acid salt.

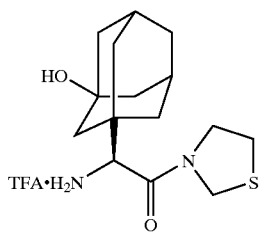

The Step 1 compound (72.0 mg, 0.18 mmol) was dissolved in TFA/CH$_2$Cl$_2$ (1:1, v/v, 1.4 mL) and stirred at rt. After 1 h, the solvents were removed by rotary evaporation and the remainder chased with toluene (2×8 mL) and Et$_2$O (2×20 mL). Preparative HPLC afforded the title compound as a white solid (56.2 mg, 76%): MS m/e 297 (m+H)$^+$.

EXAMPLE 3

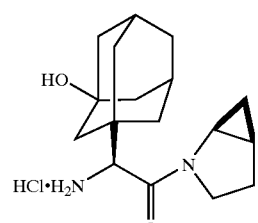

EXAMPLE 3

Step 1. N-Cbz-2-methoxypyrrolidine.

To a solution of (S)-(−)-N-benzyloxycarbonylproline (10 g, 40 mmol) in $CH_2Cl_2$ (500 mL) was added iodobenzene diacetate (26 g, 80 mmol, 2.0 equiv) and iodine (5.2 g, 20 mmol, 0.50 equiv). The resulting mixture was stirred at rt for 5 h. Methanol (20 mL) was added and the reaction mixture was stirred at rt for 1.5 h. The reaction was then quenched by the addition of 10% $Na_2S_2O_3$ (200 mL) and extracted with $CH_2Cl_2$ (2×100 mL). The combined organic extracts were washed with 10% $Na_2S_2O_3$ (200 mL), brine (200 mL), dried ($Na_2SO_4$) and concentrated under reduced pressure to give the crude product (28 g) as a yellow oil. Purification by flash chromatography (silica gel, 10–30% EtOAc/hexane) provided the expected product (9.41 g, 77%) as a yellow oil along with the corresponding hydroxy product (8.85 g, 11%) as a white solid: mp 44–46° C. The hydroxy product could subsequently be quantitatively recycled to the desired methoxy compound by treatment with pyridinium p-toluene sulfonate (PPTS) in MeOH at rt for 20 h. Data for step 1 compound: HPLC (Phenominex 4.6×50 mm) retention time 2.94 min; LC/MS m/z 236 [M+H]$^+$; $^1$H NMR (400 MHz, $CDCl_3$) δ 7.27–7.39 (m, 5H), 5.15–5.29 (m, 3H), 3.52 (td, 1H, J=8.8, 1.3 Hz), 3.32–3.48 (m, 3H), 3.26 (s, 1H), 1.99–2.15 (m, 1H), 1.84–1.98 (m, 2H), 1.67–1.82 (m, 1H). Data for compound 3: LC/MS m/z 222 [M+H]$^+$; $^1$H NMR ($CDCl_3$, 400 MHz) δ 7.30–7.40 (m, 5H), 5.47–5.55 (m, 1H), 5.15 (s, 2H), 3.55–3.65 (m, 1H), 3.30–3.42 (m, 1H), 1.78–2.02 (m, 4H).

EXAMPLE 3

Step 2. N-Cbz-2-pyrrolidine.

A solution of methoxy Step 1 compound (2.48 g, 10.5 mmol) in $CH_2Cl_2$ (30 mL) was cooled to 0° C. and treated with N,N-diisopropylethylamine (2.50 mL, 14.3 mmol, 1.36 equiv) followed by TMSOTf (2.50 mL, 13.8 mmol, 1.31 equiv). The reaction mixture was stirred at 0° C. for 30 min, then diluted with pentane (60 mL), stirred for 5 min and filtered. The filter cake was washed with pentane (2×60 mL) and $Et_2O$ (2×60 mL). The filtrate was then concentrated under reduced pressure to give a dark gold oil (2.73 g) which was purified by flash chromatography (silica gel, 1:2 $Et_2O$:hexane) to provide the desired product (1.73 g, 81%) as a colorless liquid. HPLC (Phenominex ODS 4.6×50 mm) retention time 3.14 min (99.5%); LC/MS m/z 204 [M+H]$^+$; $^1$H NMR ($CDCl_3$, 400 MHz) δ 7.27–7.38 (m, 5H), 6.57 (d, 1H, J=24.1 Hz), 5.17 (s, 2H), 5.05 (d, 1H, J=21.5 Hz), 3.78 (ABq, 2H, J=10.7, 9.4 Hz), 2.60–2.68 (m, 2H).

EXAMPLE 3

Step 3. N-Cbz-2,3-methanopyrrolidine.

To a solution of Step 2 olefin (4.99 g, 24.5 mmol) in $Et_2O$ (164 mL) at 0° C. was slowly added diethylzinc (116 mL of a 1.0 M solution in hexane, 116 mmol, 4.75 equiv), followed by $ICH_2Cl$ (17.1 mL, 235 mmol, 9.58 equiv). The resulting reaction mixture was stirred at 0° C. for 6 h, kept at −40° C. overnight and then stirred at rt for 4 h. The reaction was then quenched by the addition of 25% $NH_4Cl$ (65 mL) and extracted with $Et_2O$ (3×300 mL). The combined organic extracts were washed with 25% $NH_4Cl$ (65 mL), brine (65 mL), dried ($Na_2SO_4$), filtered and concentrated under reduced pressure to give the crude product (15 g) as a yellow oil. Purification of the crude product by flash chromatography (silica gel, $CH_2Cl_2$) generated the cyclopropyl product (4.17 g, 78%) as a colorless liquid: LC/MS m/z 218 [M+H]$^+$; $^1$H NMR ($CDCl_3$, 400 MHz) δ 7.26–7.37 (m, 5H), 5.30 (s, 2H), 3.73 (t, 1H, J=8.8 Hz), 3.45–3.55 (m, 1H), 3.03–3.10 (m, 1H), 2.05–2.15 (m, 1H), 1.91–1.97 (ddd, 1H, J=12.8, 8.4, 2.6 Hz), 1.51–1.59 (dt, 1H, J=14.1, 5.7 Hz), 0.68–0.76 (m, 1H), 0.53–0.58 (m, 1H).

EXAMPLE 3

Step 4. 2,3-Methanopyrrolidine HCl salt.

A mixture of the Step 3 compound (160 mg, 0.74 mmol), 1 N HCl (0.8 mL, 0.8 mmol, 1.08 equiv) and 10% Pd/C (32 mmol, 43 equiv) in 95% EtOH (13 mL) was stirred at rt under hydrogen atmosphere for 19 h. Another 20 mg of 10% Pd/C was added and the mixture was stirred under hydrogen atmosphere for additional 6 h. The reaction mixture was diluted with EtOH (10 mL) and filtered on a celite pad. The filtrates were concentrated under reduced pressure to give the HCl salt of expected product (95 mg, 79%) as a white solid: $^1$H NMR ($D_2O$, 400 MHz) δ 3.30 (dt, 1H, J=12.8, 5.1 Hz), 3.15 (ddd, 1H, J=6.0, 5.8, 2.9 Hz), 2.76 (q, 1H, J=9.9 Hz), 1.97–2.06 (m, 2H), 1.67–1.75 (m, 1H), 0.68–0.76 (m, 2H).

Alternatively, the 2S,3R-stereoisomer of 2,3-methanopyrrolidine can be obtained in optically pure form by a formal deamidation of the corresponding amide intermediate, as follows:

EXAMPLE 3

Step 1a. N-Benzyl-(L)-cis-4,5-methanoprolineamide.

To a solution of (L)-cis-4,5-methanoprolinamide (17.8 g, 0.11 mol) and N,N-diisopropylethylamine (57.4 mL, 0.33 mol, 3.00 equiv) in $CH_2Cl_2$ (250 mL) was slowly added benzyl bromide (14.4 mL, 0.12 mol, 1.10 equiv) at rt, and the mixture was then stirred at rt for 4 days. The solvent was evaporated and the residue was purified by flash chromatography (silica gel, 0–40% EtOAc/hexane) to generate the desired product (21.4g, 90%) as a white solid:
$^1$H NMR ($CDCl_3$, 400 MHz) δ 7.24–7.36 (m, 5H), 5.23 (br, exch), 3.84 (d, 1H, J=13.1 Hz), 3.66 (d, 1H, J=13.1 Hz), 3.50 (dd, 1H, J=10.1, 2.2 Hz), 2.63 (ddd, 1H, J=7.5,5.3,2.6 Hz), 2.26 (dd, 1H, J=12.7,2.4 Hz), 2.12–2.20 (m, 1H), 1.47 (td, 1H, J=9.2, 4.8 Hz), 0.48 (ddd, 1H, J=8.4, 8.1, 7.0 Hz), 0.24 (ddd, 1H, J=7.0, 4.0, 3.1 Hz).

EXAMPLE 3

Step 2a. N-Benzyl-(L)-cis-4,5-methanoprolinenitrile.

To a solution of the Step 1a compound (17 g, 79 mmol) in $CH_2Cl_2$ (200 mL) at 0° C. was added $NEt_3$ (22 mL, 160 mmol, 2.0 equiv), followed by the addition of TFAA (22 mL, 160 mmol, 2.0 equiv) over 15 min. Another 15 mL of $NEt_3$ was added and the resulting mixture was stirred at 0° C. for 2 h. The reaction was then quenched by the addition of 10% $Na_2CO_3$ (70 mL) and water (150 mL). The organic layer was separated and the aqueous layer was extracted with $CH_2Cl_2$ (2×150 mL). The combined organic layers were washed with brine (200 mL), dried ($Na_2SO_4$), filtered and concentrated under reduced pressure to give a brown oil. The crude product was placed on a silica gel column (silica gel, 800 g) and eluted with hexane (1.5 L), 1:1 $CH_2Cl_2$/hexane (1.2 L), $CH_2Cl_2$ (1 L), 40% EtOAc/hexane (2 L) and EtOAc (1 L) to afford the nitrile (35.5 g, 67%) as a dark burgundy-colored oil: $^1$H NMR ($CD_3OD$, 400 MHz) δ 7.35 (d, 2H, J=7.2 Hz), 7.28 (t, 2H, J=7.2 Hz), 7.22 (t, 2H, J=7.2 Hz), 391–3.97 (m, 2H), 3.81 (d, 1H, J=12.7 Hz), 2.74 (td, 1H, J=6.1, 2.8 Hz), 2.37 (ddd, 1H, J=13.8, 9.4, 4.9 Hz), 2.17 (d, 1H, J=13.1 Hz), 1.45–1.52 (m, 1H), 1.09 (ddd, 1H, J=6.6, 4.4, 2.7 Hz), 0.32 (dd, 1H, J=14.8, 6.6 Hz).

EXAMPLE 3

Step 3a. N-Benzyl-(2S,3R)-2,3-methanopyrrolidine.

To a solution of the Step 2a nitrile (11.2 g, 56 mmol) in 3:1 EtOH/$H_2O$ (400 mL) was added $NaBH_4$ (42.8 g, 113 mmol, 2.00 equiv) in portions, and the mixture was stirred at rt under nitrogen for 18 h. The solid was then removed by filtration and the filtrate was extracted with $CH_2Cl_2$ (1000 mL). The organic extract was dried ($Na_2SO_4$), filtered and concentrated under reduced pressure to give a yellow oil. Purification by flash chromatography (120 g Isco silica gel column, 5% MeOH/$CH_2Cl_2$) afforded des-cyano compound (5.79 g, 60%) as a yellow oil: $^1$H NMR ($CD_3OD$, 400 MHz) δ 7.35 (d, 2H, J=7.2 Hz), 7.29 (t, 2H, J=7.2 Hz), 7.24 (t, 1H, J=7.2 Hz), 4.88 (s, 2H), 2.78 (dd, 1H, J=9.9, 8.3 Hz), 2.56–2.70 (m, 1H), 2.03 (dt, 1H, J=10.5, 7.2 Hz), 1.91–1.98 (m, 1H), 1.85 (dd, 1H, J=12.0, 7.1 Hz), 1.43 (ddd, 1H, J=10.5, 8.8, 4.4 Hz), 0.78 (ddd, 1H, J=6.1, 3.9, 3.8 Hz), 0.17 (dt, 1H, J=7.7, 6.1 Hz).

EXAMPLE 3
Step 4a. (2S,3R)-Methanopyrrolidine.

To a solution of the Step 3a methanopyrrolidine (10.6 g, 61.2 mmol) in $CH_2Cl_2$ (100 mL) was slowly added 1-chloroethyl chloroformate (8.6 mL, 80 mmol, 1.3 equiv) at rt under nitrogen, and the reaction was stirred at rt for 10 min and then heated at reflux for 17 h. The mixture was then cooled to rt and MeOH (100 mL) was added. The resulting mixture was heated at reflux for 2 h. The solvent was removed under reduced pressure and the residue was triturated with $CH_2Cl_2/Et_2O$ several times to afford the desired compound as the HCl salt (6.6 g, 90%) as an off-white solid: $^1$H NMR (400 MHz, $CD_3OD$) 3.36–3.43 (m, 1H), 3.27–3.34 (m, 1H), 2.84–2.94 (m, 1H), 2.12–2.19 (m, 2H), 1.80–1.86 (dt, 1H, J=13.7, 4.9 Hz), 0.92 (ddd, 1H, J=7.2, 4.9, 2.8 Hz), 0.85 (dd, 1H, J=15.9, 7.2 Hz).

EXAMPLE 3
Step 5. (2S,3R)-1-[(2S)-N-Boc-2-(3-hydroxyadamant-1-yl)glycinyl]-2,3-methanopyrrolidine.

Method A from Example 3, Step 4 compound: To a mixture of the Example 1, Step 8 acid (156.7 mg, 0.48 mmol), the Step 4 amine (60 mg, 0.51 mmol, 1.06 equiv) and PyBOP (456 mg, 0.88 mmol, 1.83 equiv) in $CH_2Cl_2$ (4.5 mL) was added N-methylmorpholine (0.16 mL, 1.5 mmol, 3.1 equiv) and the mixture was stirred at rt for 20 h. The reaction was then quenched with 5% $KHSO_4$ (4.8 mL) and extracted with $CH_2Cl_2$ (2×50 mL). The combined organic layers were washed with brine (8 mL), dried ($Na_2SO_4$) and concentrated under reduced pressure. Purification by flash chromatography (35 g Isco silica gel column, EtOAc/hexane gradient) afforded a mixture of amides (114 mg) as a white solid. Separation of the isomers by chiral column chromatography (Chiralpak AD column, 15% IPA/hexane isocratic) generated the corresponding separated amides A (41.6 mg, 40.6%) and B (31.2 mg, 27.4%). Data for isomer A: Chiral HPLC (Zorbax SB C18 4.6×75 mm, linear gradient over 8 min) retention time 7.23 min (purity 92%, 100% ee); Chiral analytical HPLC (Daicel chiralcel AD 4.6×250 mm, 15% IPA/hexane) retention time 10.98 min (100% ee); LC/MS m/z 218 [M+H]$^+$; $^1$H NMR ($CDCl_3$, 400) 67 5.35 (d, 1H, J=9.9 Hz) 4.48 (d, 1H, J=9.9 Hz), 3.99 (ddd, 1H, J=13.2, 10.6, 3.3 Hz), 3.58–3.65 (m, 1H), 3.03 (dt, 1H, J=12.8, 8.8 Hz), 2.22 (bs, 1H), 2.07–2.17 (m, 1H), 1.96 (ddd, 1H, J=12.5, 8.8, 3.3 Hz) (m, 23H), 1.24–1.28 (m, 1H), 0.86–0.90 (m, 1H), 0.57–0.62 (td, 1H, J=5.5, 2.6 Hz). Data for isomer B: HPLC (Zorbax SB C18 4.6×75 mm, linear gradient over 8 min) retention time 7.22 min (96%); Chiral analytical HPLC (Daicel chiralcel AD 4.6×250 mm, 15% IPA/hexane) retention time 14.12 min (100% ee).

Method B from EXAMPLE 3 Step 4a compound: A mixture of the acid of Example 1, Step 8 (96 mg, 0.30 mmol), amine of Step 4a (35 mg, 0.29 mmol, 0.97 equiv), PyBOP (236.1 mg, 0.45 mmol, 1.5 equiv) and N-methylmorpholine (0.09 mL, 0.84 mmol, 2.8 equiv) in $CH_2Cl_2$ (2.5 mL) was stirred at rt for 20 h. The reaction was then quenched by the addition of 5% $KHSO_4$ (3 mL) and extracted with $CH_2Cl_2$ (2×80 mL). The combined organic extracts were washed with brine (5 mL), dried ($Na_2SO_4$), filtered and concentrated under reduced pressure to give a yellow oil. Purification by flash chromatography (35 g Isco silica gel column, EtOAc/hexane gradient followed by $CH_2Cl_2$/MeOH gradient) afforded amide isomer A (110.5 mg, 97.5%) as a yellow oil: LC/MS m/z 391 [M+H]$^+$; HPLC (Zorbax SB C18 4.6×75 mm, linear gradient over 8 min) retention time 7.23 min (99%); Chiral analytical HPLC (Daicel chiralcel AD 4.6×250 mm, 15% IPA/hexane) retention time 10.74 min (100% ee).

EXAMPLE 3
Step 6. (2S,3R)-1-[(2S)-2-(3-hydroxyadamant-1-yl)glycinyl]-2,3-methanopyrrolidine.

To a solution of the amide of Step 5 (7.20 g, 18.5 mmol) in $CH_2Cl_2$ (50 mL) was added a solution of 4 N HCl in dioxane (35 mL, 140 mmol, 7.5 equiv) and the resulting mixture was stirred at rt for 75 min. The reaction mixture was then concentrated under reduced pressure and the residue was sequentially triturated with 1:5 $CH_2Cl_2/Et_2O$ (120 mL) and $Et_2O$ ether (100 mL). Evaporation of the volatiles followed by lyophilization from $H_2O$ gave the HCl salt of the desired compound (6.3 g, 91%, based on 1.33 $H_2O$ and 1.64 HCl) as a white solid: HPLC (Phenominex Luna 3μ C18 4.6×150 mm, 95% A to 95% B (A=$H_2O$+ 0.05% TFA, B=Acetonitrile+0.05% TFA, flow rate 1 mL/min, linear gradient over 42 min) retention time 13.37 min (97.9%); Chiral analytical HPLC (Chiralpak AD 10μ 4.6×250 mm, 80% heptane+20% 1:1 EtOH:MeOH+0.1% DEA, flow rate 1 mL/min, isocratic) retention time 10.56 min (98.2% ee); LC/MS m/z 291 [M+H]$^+$; $^1$H NMR ($D_2O$) δ 4.16 (s, 1H), 3.82 (ddd, 1H, J=13.2, 10.3, 2.9 Hz), 3.48 (td, 1H, J=6.2, 2.6 Hz), 2.94 (dt, 1H, J=13.1, 8.7 Hz), 2.14 (bs, 2H), 1.94–2.05 (m, 1H), 1.88 (ddd, 1H, J=12.4, 8.4, 3.3 Hz), 1.74 (ddd, 1H, J=8.8, 11.4, 5.2), 1.3–1.73 (m, 12H), 0.74–0.85 (m, 1H), 0.65–0.71 (td, 1H, J=5.7, 2.6); $^{13}$C NMR ($D_2O$, 400 MHz) δ 167.3, 69.1, 59.6, 45.3, 45.1, 43.1, 39.7, 38.2, 37.1, 36.8, 36.6, 34.5, 30.2, 30.1, 24.4, 18.9, 12.8; Anal. Calcd for $C_{18}H_{25}N_3O_3$•1.64 HCl•1.33 $H_2O$: C, 54.56; H, 8.16; N, 7.49; Cl, 15.57. Found: C, 54.42; H, 7.86; N, 7.35; Cl, 15.57. KF, 6.39.

EXAMPLE 4

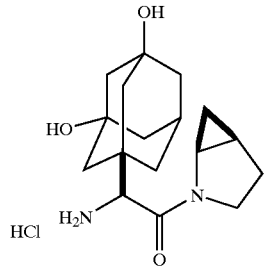

EXAMPLE 4
Step 1. (S)-N-Boc-3,5-Dihydroxyadamantylglycine.

Refer to the procedure of Example 1, Step 8 that generates hydroxyadamantyl-N-tert-butyloxycarbonyl-L-glycine. During the reaction, the diol is formed as a lower Rf minor product. Slightly longer reaction times (up to 90 min) gave up to 17% of the diol in addition to the Example 1, Step 8 compound. With the procedure identical in every other respect, the diol is obtained as a white solid, after chasing with hexanes, by flushing the column with 15% MeOH-CH$_2$Cl$_2$-0.5% HOAc. $^1$H NMR (500 MHz, CD$_3$OD) 1.41–1.73 (m, 21H), 2.29 (br s, 1H), 3.95 (s, 1H). $^{13}$C NMR (125 MHz, CD$_3$OD) 174.2, 157.9, 80.6, 71.0, 70.9, 63.1, 52.5, 49.6, 48.3, 46.3, 43.9, 41.8, 37.5, 31.8, 28.7.

EXAMPLE 4

Step 2. (2S,3R)-1-[(2S)-N-Boc-2-(3,5-dihydroxyadamant-1-yl)glycinyl]-2,3-methanopyrrolidine.

Method A: To a mixture of the acid of Step 1 (163.5 mg, 0.48 mmol), amine of Example 3, Step 4 (67.0 mg, 0.56 mmol, 1.16 equiv) and PyBOP (456 mg, 0.88 mmol, 1.83 equiv) in anhydrous CH$_2$Cl$_2$ (4.5 mL) was added N-methylmorpholine (0.16 mL, 1.5 mmol, 3.1 equiv), and the mixture was stirred at rt for 24 h. The reaction mixture was then partitioned between 5% KHSO$_4$ (4.8 mL) and CH$_2$Cl$_2$ (2×50 mL). The combined organic layers were washed with brine (8 mL), dried (Na$_2$SO$_4$), filtered and concentrated under reduced pressure. Purification by flash chromatography (35 g Isco silica gel column, CH$_2$Cl$_2$/MeOH gradient) afforded 150 mg (76.8%) of a mixture of amides A and B as a white solid. Separation by chiral column chromatography (Chiralcel OD column, 3% IPA/hexane isocratic) afforded amide A (42.7 mg, 21.9%) and amide B (22 mg, 11.3%) as white solids. For isomer A: HPLC (Zorbax SB C18 4.6×75 mm, linear gradient over 8 min) retention time 5.96 min (99%); Chiral analytical HPLC (Daicel chiralcel OD 4.6×250 mm, 3% IPA/hexane isocratic) retention time 43.34 min (100% ee); LC/MS m/z 407 [M+H]$^+$; $^1$H NMR (CDCl$_3$, 400 MHz) δ 5.37 (d, 1H, J=9.7 Hz), 4.56 (d, 1H, J=9.7 Hz), 3.99 (ddd, 1H, J=13.2, 10.6, 3.1 Hz) 3.61 (td, 1H, J=6.2, 2.3 Hz), 3.04 (dt, 1H, J=13.2, 8.8 Hz), 2.37 (dddd, 1H, J=3.1, 3.1, 3.1, 3.1 Hz), 2.05–2.25 (m, 1H), 1.97 (ddd, 1H, J=12.3, 8.8, 3.1 Hz), 1.20–1.80 (m, 22H), 0.86–0.92 (m, 1H), 0.57–0.63 (td, 1H, J=5.7, 2.6 Hz). For isomer B: HPLC (Zorbax SB C18 4.6×75 mm, linear gradient over 8 min) retention time 5.96 min (99%); LC/MS m/z 407 [M+H]$^+$; Chiral analytical HPLC (Daicel chiralcel OD 4.6×250 mm, 3% IPA/hexane isocratic) retention time 38.8 min (100% ee). Method B from Example 3, Step 4a compound: A mixture of acid of Step 1 (86 mg, 0.25 mmol), amine of Example 3, Step 4a (30 mg, 0.25 mmol, 1.0 equiv), PyBOP (202.3 mg, 0.38 mmol, 1.5 equiv) and N-methylmorpholine (0.08 mL, 0.73 mmol, 2.9 equiv) in CH$_2$Cl$_2$ (2.0 mL) was stirred at rt for 20 h. The reaction mixture was quenched with the addition of 5% KHSO$_4$ (2.5 mL) and extracted with CH$_2$Cl$_2$ (2×25 mL). The combined organic extracts were washed with brine (4 mL) dried (Na$_2$SO$_4$), filtered and evaporated to give a foam. Purification by flash chromatography (35 g Isco silica gel column, CH$_2$Cl$_2$/MeOH gradient) afforded amide A (92.6 mg, 89.9%) as a white foam: LC/MS m/z 407 [M+H]$^+$; Chiral analytical HPLC (Daicel chiralcel OD 4.6×250 mm, 3% IPA/hexane isocratic) retention time 43.86 min (100% ee).

EXAMPLE 4

Step 3. (2S,3R)-1-[(2S)-2-(3,5-dihydroxyadamant-1-yl) glycinyl]-2,3-methanopyrrolidine.

A mixture of the amide of Step 2 (39.3 mg, 0.097 mmol), TFA (0.15 mL) and CH$_2$Cl$_2$ (0.15 mL) was stirred at rt for 1 h. The reaction mixture was then diluted with CH$_2$Cl$_2$ (1.9 mL) and concentrated under reduced pressure to give the crude product. Trituration of the crude product with Et$_2$O (2×1 mL) afforded the desired compound (39.1 mg, 96.1%) as a white solid: HPLC (Phenominex 4.6×50 mm) retention time 1.08 min (100%); LC/MS m/z 307 [M+H]$^+$; $^1$H NMR (D$_2$O, 400 MHz) δ 4.65 (s, 1H), 4.29 (ddd, 1H, J=13.2, 10.6, 2.6 Hz), 3.85–3.93 (m, 1H), 3.40 (dt, 1H, J=13.2, 8.8 Hz), 2.72 (d, 1H, J=3.1), 2.38–2.49 (m, 1H), 2.6–2.37 (m, 1H), 2.14–2.24 (m, 1H), 1.70–2.60 (m, 15H), 1.18–1.30 (m, 1H), 0.97–1.04 (m, 1H); LRMS (ES$^+$) 307.0, 329.0, 613.2, 635.2; HRMS calcd for: C$_{17}$H$_{26}$N$_2$O$_3$ 307.2022; Found: 307.2025.

EXAMPLE 5

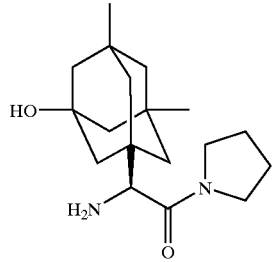

EXAMPLE 5

Step 1.

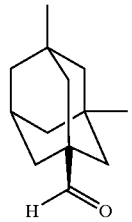

To a solution of 3,5-dimethyl-1-adamantane carboxylic acid (6.0 g, 28.8 mmol) in THF (150 mL) at rt was slowly added lithium aluminum hydride (1.0 M in THF, 30 mL, 30 mmol) over 10 min. Thr reaction was exothermic during the addition and the reaction temperature approached 60° C. The reaction was cooled to rt and stirred for 3 h. Saturated Na$_2$SO$_4$ (~5 mL) was very carefully added dropwise over 20 min until no further gas evolution was observed. The reaction was then diluted with Et$_2$O (200 mL), solid Na$_2$SO$_4$ (10 g) was added and the reaction was stirred vigorously for 2 h. Solids were removed by filtration and were rinsed twice with Et$_2$O. The combined eluent was reduced under vacuum to give the crude 3,5-dimethyladamant-1-yl)methanol as a light yellow oil which solidified on standing.

To a solution of DMSO (4 mL, 57.7 mmol) in DCM (125 mL) under nitrogen at –78° C. was added dropwise oxalyl chloride (2.0 M in DCM, 18.75 mL, 37.5 mmol) over 30 min. After final addition the reaction mixture was stirred at –78° C. for 30 min. With the reaction mixture still at –78° C., a solution of crude (3,5-dimethyladamant-1-yl)methanol from above in DCM (50 mL) was added dropwise over 20 min. After stirring the reaction at –78° C. for 2 h, Et$_3$N (15 mL) was added slowly over 10 min and the reaction was stirred for 30 min at –78° C. Saturated NaH$_2$PO$_4$ (15 mL) was added followed by water (150 mL), and the reaction was then warmed to rt. The DCM layer was separated, washed twice with 1N HCl and sat'd NaHCO$_3$, dried over MgSO$_4$, filtered and concentrated to give the step 1 compound, 3,5-dimethyladamantane-1-carboxaldehyde (5.58 g).

EXAMPLE 5
Step 2.

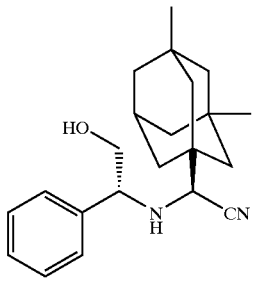

To a rt solution of 3,5-dimethyladamantane-1-carboxaldehyde (5.58 g, 29 mmol) in methanol (28 mL) and water (75 mL) was added (R)-(−)-2-phenylglycinol (3.98 g, 29 mmol), KCN (1.97 g, 30.16 mmol) and NaHSO$_3$ (3.02 g, 29 mmol). The reaction was then heated at 100° C. for 16 h, cooled to rt, diluted with EtOAc (200 mL) and stirred vigorously for 15 min. The layers were separated and the organic layer was washed twice with water and once with brine. The organics were dried over Na$_2$SO$_4$, filtered and concentrated to provide the step 2 compound (8.5 g). (M+H)$^+$=339.12

EXAMPLE 5
Step 3.

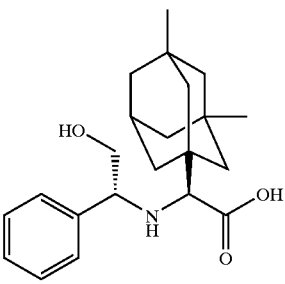

The Step 2 compound (8.5 g) was taken up in conc. HCl (100 mL):HOAc (15 mL) and heated at 80° C. for 18 h. The reaction was cooled to rt and diluted with water (~100 mL) and an oily precipitate formed. The reaction mixture was extracted with dichloromethane (250 mL) and this extract was washed twice with water. The aqueous layers were then back extracted twice, in the order the layers were generated, with dichloromethane. The combined organic extracts were dried over MgSO$_4$, filtered and concentrated to give the step 3 compound (8.9 g) as a white solid. (M+H)$^+$=358.05

EXAMPLE 5
Step 4.

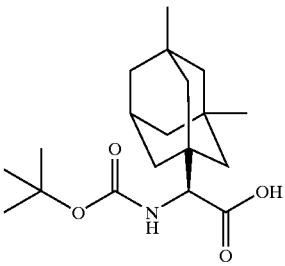

To a solution of the step 3 carboxylic acid (8.9 g) in methanol (200 mL) was added HOAc (20 mL) and Pearlman's catalyst (1.5 g). The reaction vessel was charged to 50 p.s.i. and the reaction was stirred overnight. The reaction mixture was then filtered through a plug of celite, and the plug was washed liberally with methanol. The combined eluent was concentrated under reduced pressure. The resulting residue was triturated with Et$_2$O to give (S)-(3,5-dimethyladamantan-1-yl)-glycine (4.2 g) as a white solid. This solid was taken up in DMF (75 mL) and treated with BOC$_2$O (6 mL), K$_2$CO$_3$ (6 g) and stirred overnight at rt. Solvents were removed under vacuum and the residue was partitioned between Et$_2$O (100 mL) and water (100 mL). With the pH at ~8, the water layer was washed twice with Et$_2$O. 1N HCl was added dropwise to the aqueous layer to adjust to pH ~3. The aqueous layer was then extracted twice with EtOAc and twice with dichloromethane. The combined organics were dried over MgSO$_4$, filtered and concentrated to provide the step 4 compound, N-BOC-(3,5-dimethyladamantan-1-yl)-glycine (3.83 g) as a white solid. MS m/e (M+H)$^+$=338.1

EXAMPLE 5
Step 5.

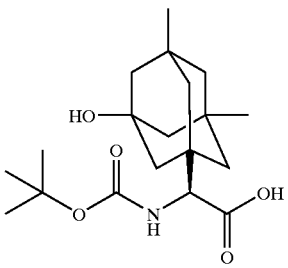

To a solution of N-BOC-(3,5-dimethyladamantan-1-yl)-glycine (1.79 g, 5.3 mmol) in 2% KOH/water (75 mL) at rt was added KMnO$_4$ (1.0 g, 6.3 mmol). The reaction was heated to 90° C. for 2 h. An additional portion of KMnO$_4$ (0.3 g, 1.9 mmol) was added and the reaction was heated at 90° C. for an additional 1.5 h. The reaction was then diluted with EtOAc (150 mL) and with vigorous mixing the pH was addjusted to ~3 with 1N HCl. The EtOAc layer was separated and set aside. The aqueous layer was then extracted once more with EtOAc and twice with dichloromethane. The combined organics were dried over MgSO$_4$, filtered and concentrated to give N-BOC-(3-hydroxy-5,7-dimethyladamant-1-yl)-glycine (1.91 g). MS m/e (M+H)$^+$=354.2

EXAMPLE 5
Step 6.

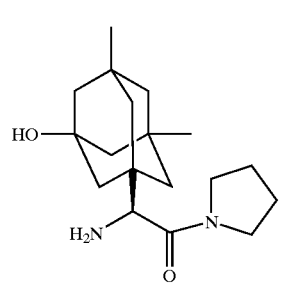

To a solution of N-BOC-(3-hydroxy-5,7-dimethyladamant-1-yl)-glycine (113 mg, 0.320 mmol) in dichloromethane (3 mL) at rt was added EDAC (113 mg) and HOBT (113 mg). The reaction was stirred at rt for 10 min, and then pyrrolidine (100 μL) was added. After stirring overnight at rt the reaction was diluted with EtOAc, washed twice with 1N HCl and once with NaHCO$_3$. The organics were dried over MgSO$_4$, filtered and concentrated. The residue was taken up in dichloromethane (2 mL) and 4N HCl in dioxane (2 mL) and stirred for 2 h at rt. Solvent was removed and purification by reverse-phase preparative HPLC provided (3-hydroxy-5,7-dimethyladamant-1-yl)-glycine pyrrolidine amide (92 mg). MS m/e (M+H)$^+$=307.3.

EXAMPLE 6

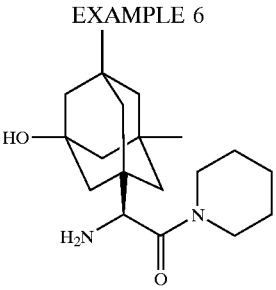

EXAMPLE 6

Step 1.

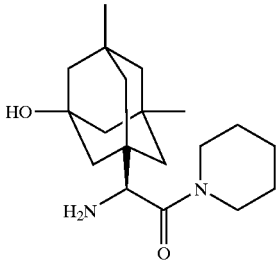

To a solution of Example 5; Step 5 compound, N-BOC-(3-hydroxy-5,7-dimethyladamant-1-yl)-glycine (40 mg, 0.113 mmol) in dichloromethane (3 mL) at rt was added EDAC (40 mg) and HOBT (40 mg). The reaction was stirred at rt for 10 min and then piperidine (50 µL) was added. After stirring overnight at rt the reaction was diluted with EtOAc, washed twice with 1N HCl and once with sat'd NaHCO$_3$. The organics were dried over MgSO$_4$, filtered and concentrated. The residue was taken up in dichloromethane (2 mL) and 4N HCl in dioxane (2 mL) and stirred for 2 h at rt. The solvent was removed, and purification by reverse-phase preparative HPLC provided (3-hydroxy-5,7-dimethyladamant-1-yl)-glycine piperidine amide (92 mg). MS m/e (M+H)$^+$=321.3.

EXAMPLE 7

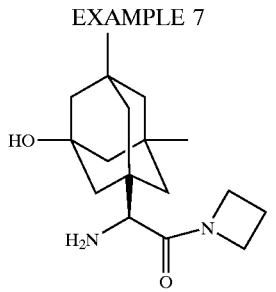

This compound was prepared from N-BOC-(3-hydroxy-5,7-dimethyladamant-1-yl)-glycine and azetidine in a manner similar to that previously described for Example 6 to provide (3-hydroxy-5,7-dimethyladamant-1-yl)-glycine azetidine amide. MS m/e (M+H)$^+$=292.2.

EXAMPLE 8

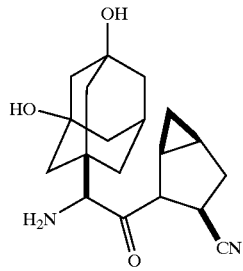

EXAMPLE 8

Step 1. (S)-3,5-Dihydroxyadamantylglycine-L-cis-4,5-methanoprolinenitrile TFA salt.

A coupling reaction between Example 4 Step 1 compound (300 mg, 0.88 mmol, 1 equiv) and L-cis-4,5-methanoprolinamide (253 mg, 1.05 mmol, 1.2 equiv) was carried out using HOBT (356 mg, 2.64 mmol, 3.0 equiv), EDAC (340 mg, 1.76 mmol, 2.0 equiv), and TEA (0.37 mL, 2.64 mmol, 3.0 equiv). the product was purified on SiO$_2$ flash column with a gradient of 10–20% MeOH/CH$_2$Cl$_2$ to give the coupled amide that was contaminated with HOBT. This impure material was brought on immediately to the dehydration reaction in two separate reactions. In each reaction, the amide (100 mg, 0.11 mmol) was dissolved in 1 mL THF and cooled to 0° C. and to the reaction was added pyridine (0.054 mL, 0.66 mmol, 6 equiv) followed by addition of trifluoroacetic anhydride (0.056 mL, 0.39 mmol, 3.5 equiv). No starting material was seen by TLC (SiO$_2$, 7% MeOH/CH$_2$Cl$_2$) after 30 min. The solvent was removed and the intermediate trifluoroacetate nitrile was hydrolyzed by stirring with 10% K$_2$CO$_3$ (1 mL) in MeOH (2 mL) at rt for 18 h. The two reactions appeared comparable and were combined. The MeOH was removed and the aqueous layer was extracted with EtOAc (2×20 mL). The extracts were dried (Na$_2$SO$_4$), filtered, concentrated, and purified by flash chromatography with a gradient of 7–8% MeOH/CH$_2$Cl$_2$ to afford the nitrile (78 mg, 41%) over two steps as a white foam. $^1$H NMR (500 MHz, CDCl$_3$) 1.01–1.06 (m, 2H), 1.32–1.78 (m, 22H, includes N-Boc singlet), 1.85–1.91 (m, 1H), 2.06 (bs, 2H), 2.34–2.38 (m, 2H), 2.52–2.59 (m, 1H), 3.80–3.84 (m, 1H), 4.52 (d, J=9.9, 1H), 5.0 (dd, J=10.6, 2.2, 1H), 5.46 (d, J=9.9, 1H). $^{13}$C NMR (125 MHz, CDCl$_3$) 169.8, 155.8, 119.2, 80.1, 70.4, 58.0, 51.9, 45.3, 45.2, 45.1, 43.1, 42.9, 42.6, 38.0, 36.3, 30.4, 28.4, 17.9, 13.7. MS (FAB) m/z 432 [M+H]$^+$.

EXAMPLE 8

Step 2.

The nitrile of Step 1 (64 mg, 0.15 mmol) was deprotected using TFA according to the procedure described in Example 1, Step 10. The solvents were removed after 2.5 h and the resulting oil was chased with CH$_2$Cl$_2$/toluene (2×) to obtain an off-white solid. Purification by preparative HPLC [YMC S5ODS 30 mm×100 mm, 15 min gradient of 0 to 100% B, 25 mL/min. 220 nm, A=10% MeOH-90% H$_2$O-0.1% TFA and B=90% MeOH-10% H$_2$O-0.1% TFA, elution time 5–6 min.) afforded, after lyophillization from H$_2$O, 34 mg (53%) of the desired compound as a white lyophillate. $^1$H NMR (500 MHz, CD$_3$OD) 0.89–0.92 (m, 1H), 1.00–1.05 (m, 1H), 1.41–1.70 (m, 12H), 1.89–1.96 (m, 1H), 2.24–2.31 (m, 2H), 2.51–2.55 (m, 1H), 3.80–3.84 (m, 1H), 4.26 (s, 1H), 5.10 (dd, J=10.0, 2.2, 1H). 3.88–3.96 (m, 1H), 4.28 (s, 1H), 5.19 (d, J=10.7, 1H); 13C NMR (125 MHz, CD$_3$OD) 167.2, 120.3, 70.5, 59.4, 52.4, 47.1, 45.8, 45.7, 43.7, 43.6, 42.1, 39.3, 37.1, 31.6, 31.4,19.3,14.5. HPLC (YMC S-5 C18 4.6×50 mm, 0–100%B, MeOH/H₂O/H₃PO₄) RT=1.987 min; HRMS m/z calcd [M+H]⁺ for $C_{18}H_{25}N_3O_3$ 332.1974, found 332.1981. Anal. ($C_{18}H_{25}N_3O_3 \cdot 1.15\ CF_3CO_2H \cdot 1.50\ H_2O$) C, H, N.

EXAMPLE 9

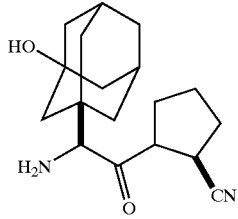

EXAMPLE 9

Step 1

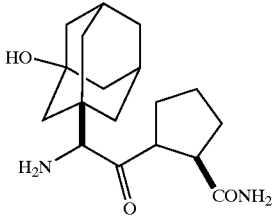

Step 1 compound was prepared by the method described in Example 1; Step 1 using Example 1; Step 8 carboxylic acid to give the title compound.

EXAMPLE 9

Step 2.

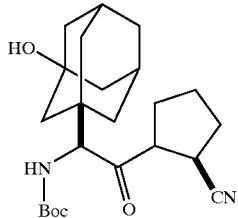

An oven-dried round bottomed flask was charged with the Step 1 compound (50 mg, 0.15 mmol), pyridine (0.5 mL), and dichloromethane sealed under nitrogen atmosphere and cooled to 0° C. Slow addition of TFAA (95 mg, 0.45 mmol) gave after mixing a thick slurry. The mixture was stirred at 0° C. for 3 h and the reaction quenched with a mixture of methanol and aqueous $K_2CO_3$. The pH=9.5 and the mixture was stirred overnight. The volatiles were evaporated, and the remainder was partitioned between a small volume of water and dichloromethane. The organic layer was dried (MgSO₄), concentrated, and purified by flash column chromatography with 95:5 to 85:15 dichloromethane/methanol to yielded 40 mg (85%) of the title compound.

EXAMPLE 9

Step 3.

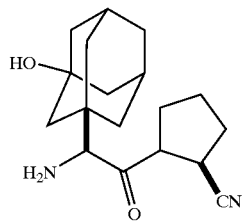

The step 3 compound was prepared using the Step 2 compound following the procedure of Example 1; step 10 to give the title compound. MS m/e (M+H)⁺ 303.3

EXAMPLES 10 TO 16

The following Examples (10–16) were prepared using methods similar to those previously described herein and/or by methods readily available to one skilled in the art.

| Example # | Structure | MS m/e [M + H]⁺ |
|---|---|---|
| 10 | 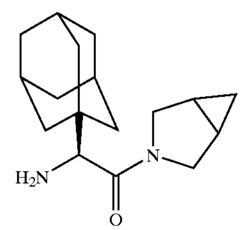 | 274.2 |
| 11 | 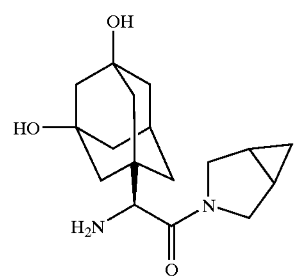 | 306.2 |
| 12 | 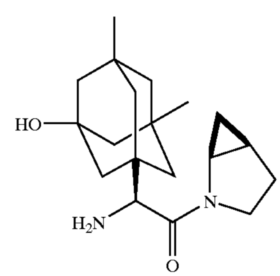 | 318.2 |
| 13 | 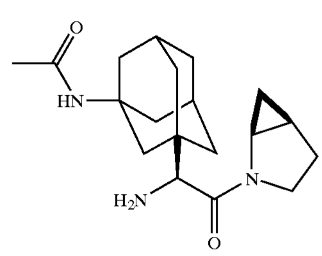 | 331.2 |

-continued

| Example # | Structure | MS m/e [M + H]+ |
|---|---|---|
| 14 | 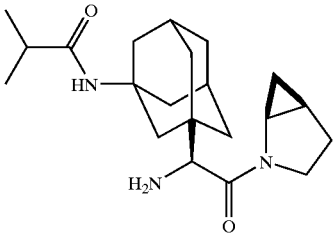 | 359.3 |
| 15 | 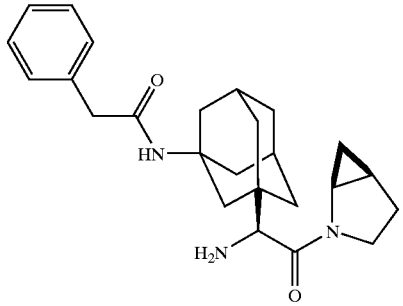 | 407.3 |
| 16 | 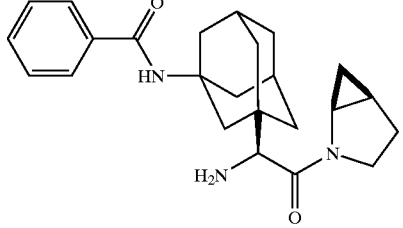 | 393.2 |

Reference Standard Compound Preparation

Reference Standard Example 1. (Ashworth, Doreen M.; Atrash, Butrus; Baker, Graham R.; Baxter, Andrew J.; Jenkins, Paul D.; Jones, D. Michael; Szelke, Michael. 4-*Cyanothiazolidides as very potent, stable inhibitors of dipeptidyl peptidase IV*. Bioorganic & Medicinal Chemistry Letters (1996), 6(22), 2745–2748.)

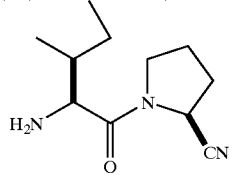

Reference Standard Example 1
Step 1.

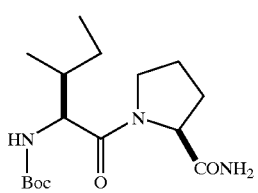

The step 1 compound was prepared using am L-(–)-prolinamide and N-tert-butoxycarbonyl-(L)-iso-leucine following the procedure of Example 11; step 1 to give the title compound.

Reference Standard Example 1
Step 2.

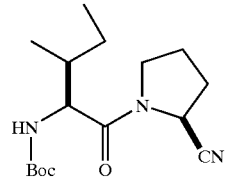

The step 2 compound was prepared using the step 1 compound following the procedure of Example 11; step 2 to give the title compound.

Reference Standard Example 1
Step 3.

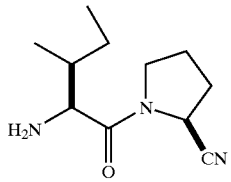

The step 3 compound was prepared using the step 2 compound following the procedure of Example 11; step 3 to give the title compound.

Reference Standard Example 2 (Pauly, Robert P.; Demuth, Hans-Ulrich; Rosche, Fred; Schmidt, Jorn; White, Heather A.; Lynn, Francis; McIntosh, Christopher H. S.; Pederson, Raymond A. *Improved glucose tolerance in rats treated with the dipeptidyl peptidase IV (CD26) inhibitor Ilethiazolidide*. Metabolism, Clinical and Experimental (1999), 48(3), 385–389.)

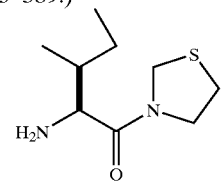

Reference Standard Example 2
Step 1.

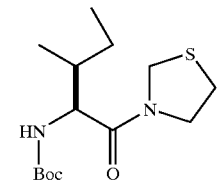

The step 1 compound was prepared using thiazolidine and N-tert-butoxycarbonyl-(L)-iso-leucine following the procedure of Example 11; step 1 to give the title compound.

Reference Standard Example 2

Step 2.

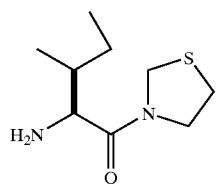

Reference Standard Example 2; step 2 compound was prepared using the step 1 compound following the procedure of Example 11; step 3 to give the title compound.

Solution Stability

Studies on proline boronic acid deptide inhibitors of dipeptidyl peptidase IV as detailed in *J. Am Chem Soc.*, 116, 10860–10869, (1994) have indicated that there is a strong correlation between the amount of β-branching in the N-terminal amino acid residue and the rate of cyclization to form a hydroxy-[1,4,2]diazaborinan-5-one ring system. This was best illustrated by changes in the solution half-lives where the AlaBP ($t_{1/2}$=0.73 h) cyclized faster than the more highly branched inhibitors ProBP ($t_{1/2}$=2.6 h) and the ValBP ($t_{1/2}$=3.1 h). As observed the greater degree of β-branching imparts a greater degree of solution stability.

Solution stability studies on 2-cyano-pyrrolidines have followed a similar trend demonstrating unique characteristics of highly branched amino acids. In experiments at pH=7.2 and 39° C., the greater degree of β-branching the greater degree of stability associated with the compound. For example, the tert-Leucine-cyanopyrrolide (11; $t_{1/2}$=27 h) is nearly 6 times more stable than the isomeric iso-Leucine-cyanopyrrolide (Ref. Std. 1; $t_{1/2}$=5 h). These effects can be understood through computational analysis where the □□H's of the most stable conformation is compared to the conformation where cyization is expected to proceed from. These are depected in the table below. As can be seen from the table below by increaseing β-branching the conformation where increased stabilty resides is reinforced. Hence the highly branched and bulky Adamantyl imparts greater stability ≧tert-butyl>iso-propyl.

group is 109°±1° while the distance between the these reactive partners is 2.95 Å. It is therefore reasonable to expect that intramolecular cyclization is initiated from such a conformation. The value of 109° between the amine group and the nitrile is in close agreement with the hypothetical angle of attack of at least 108° reported by Baxter and Connor. This angle is obtained from X-ray crystal structure data that advocate the favored direction of approach of a nucleophile to an sp carbon of a nitrile making an angle of at least 108°. Additionally, Aray and Murgich have reported a similar value of 103° based on analysis of charge density from ab initio calculations on $CH_3CN$. It was envisioned that the relative energetic differences between the global minimum and the local minimum would represent a means to validate the relative stabilities of compounds in solution.

The energies in the first column of Table 2 correspond to the difference in conformational energy between the ground state and the geometry in which the reactive amine and nitrile are in close proximity, where internal cyclization could occur, for compounds lacking the cis-methano group. The ab initio (G98) results are expected to be considerably more accurate than the force field values. The results indicate that the energy required to assume the anti conformation grows larger as the side chain bulk increases (e.g. 0.3, 1.9, 2.9 kcal/mol for no side chain, the alanine and the tert-leucine side chains, respectively). The force field energy results agree qualitatively with the ab initio values, and suggest that the primary contribution is due to van der Waals interactions. Examination of the structures reveals extremely close contacts between two of the side chain methyl groups and the carbonyl oxygen in the anti conformation (approximately 3 Å each) which would increase the difficulty for these compounds to assume the conformation required for internal cyclization, and thus lead to greater compound stability.

Conformation Energies for Cyanopyrrolidino-peptides with Branched Sidechains

Energy of Anti Relative to Syn (Ground State) Conformation

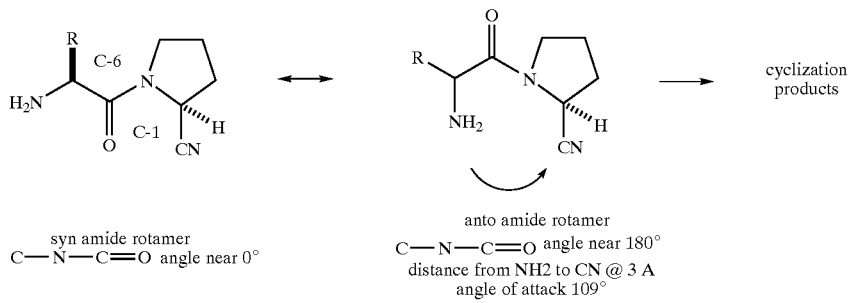

syn amide rotamer
C—N—C=O angle near 0° anto amide rotamer
C—N—C=O angle near 180°
distance from NH2 to CN @ 3 A
angle of attack 109° cyclization products

Conformations were generated for the proline forms of the N-terminal dipeptide compounds. The calculated ground state structure for the dipeptide has a conformation, characterized by a small C(1)-N—C(6)-O torsional angle at or near 0°. In addition to this configuration, there is a calculated local low energy minimum where the reactive amine and nitrile are in close proximity to each other; in this configuration the C(1)-N—C(6)-O torsional angle is near 180°. Moreover, the angle between the amine N and the C≡N

| Compound | R | ΔΔH[a] (kcal/mol) |
|---|---|---|
| Alanine | Me | 1.9 |
| Valine | Isopropyl | 2.2[b] |
| Tert-leucine | t-butyl | 2.8 |

-continued

| Compound | R | ΔΔH[a] (kcal/mol) |
|---|---|---|
| Adamantylglycine | Adamantane | 2.9 |
| Tri-methylylated Adamanylglycine | Tri-methyl-adamantane | 2.9 |

[a] Energies computed using the B3LYP DFT method and the 6 − 31 + G** basis set in Gaussian 98.0. Gaussian 98, Revision A.6, M. J. Frisch, G. W. Trucks, H. B. Schiegel, G. E. Scuseria, Robb, M. A.; Cheeseman, J. R.; Zakrzewski, V. G.; Montgomery, Jr. J. A.; Millam, J. M.; Replogle, E. S.; Pople, J. A. et. al. Gaussian, Inc.: Pittsburgh PA, 1998.
[b] Average of results for three rotamers of the valine sidechain.

The above data support the unique finding the the greater degree of β-branching the greater degree of stability imparted to the DPP-IV inhibitor nitrites.

In Vivo Evaluation

In vivo evaluation of DPP-IV inhibitors has supported the connection between DPP-IV inhibition, increases in plasma insulin levels, and an improvement in glucose tolerance.[1] Several compounds in the present series are potent inhibitors of DPP-IV in vitro. As such, these inhibitors were selected to determine the effects of DPP-IV inhibition ex vivo and on glucose tolerance in Zucker$^{fa/fa}$ rat. The Zucker$^{fa/fa}$ rat is a frequently used model in type II diabetes and obesity research. Zucker$^{fa/fa}$ rats are severely hyperphagic, extremely obese, markedly insulin resistant and mildly hyperglucemic due to a mutation and lost of function of the leptin receptor gene.[2,3] Fasted male Zucker$^{fa/fa}$ rats were dosed orally with water, or with inhibitors at (3 μmol/Kg) and an oral glucose tolerance test (OGTT) was conducted 4 h after the dosing. Plasma glucose levels were then monitored over a 2 h period. Columns 3 and 4 show the ex vivo plasma DPP-IV inhibition activity. Column 4 contians % lowering for AUC's in response to an oral glucose challenge (2 g/kg). Animals in the control group reached peak plasma glucose levels 60 min after glucose administration, at which point the drug treated animals exhibited a marked decrease in glucose levels compared to controls. Moreover, the adamantyl compounds demonstrated not only a significant improvement in inhibiting DPP-IV activity compared to the reference standards, but also demonstrated a increased control in the glucose tolerance assay. Specifically, Reference Standard 1 is has almost no inhibition in the ex vivo assay at 4 h, and gives only a slight change in glucose control when dosed at very high levels. In contrast, the adamantyl inhibitors show good inhibitory activity in the ex vivo assay, even at extended time points. As would be expected, compounds 11 and 9 show good glucose control and are more efficacious in glucose lowering than Reference Standard 1.

| Cmpd # | Structure | Ki | % Inhibition in Rat Ex Vivo assay 3 μmol/kg 0.5 h post dose | % Inhibition in Rat Ex Vivo assay 3 μmol/kg 4 h post dose | Glucose Lowering at 4 h; % AUC's, compared to control |
|---|---|---|---|---|---|
| Ref. Std 1 | 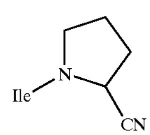 | 2 nM | 30% | 5% | −11% dosed at 16 μm/kg −19% dosed at 200 μm/kg |
| Ref. Std. 2 | 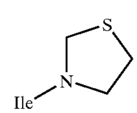 | 110 nM | 50% @ 110 umol/kg | — | — |
| Ex 8 | 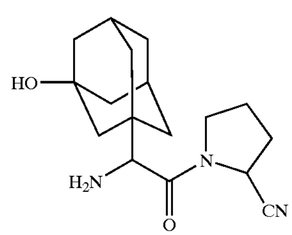 | 17 nM | 80% | 67% | |
| Ex 5 | 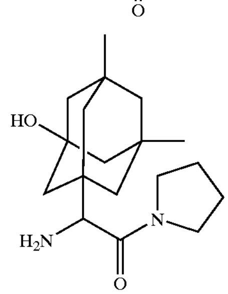 | 133 nM | 70% | 66% | −39% |

-continued

| Cmpd # | Structure | Ki | % Inhibition in Rat Ex Vivo assay 3 μmol/kg 0.5 h post dose | % Inhibition in Rat Ex Vivo assay 3 μmol/kg 4 h post dose | Glucose Lowering at 4 h; % AUC's, compared to control |
| --- | --- | --- | --- | --- | --- |

1. (a) Holst, J. J.; Deacon, C. F. Inhibition of the activity of Dipeptidyl-Peptidase IV as a treatment for Type 2 Diabetes. Diabetes, 1998, 47, 1663–1670. (b) Balkan, B.; Kwansnik, L.; Miserendino, R.; Holst, J. J.; Li, X. Inhibition of dipeptidyl peptidase IV with NVP-DPP728 increases plasma GLP-1 (7–36 amide) concentrations and improves oral glucose tolerance in obese Zucker rats. Diabetologia 1999, 42 (11), 1324–1331. (c) Rothenberg, P.; Kalbag, J.; Smith, H. T.; Gingerich, R.; Nedelman, J.; Villhauer, E.; McLeod, J.; Hughes, T. Treatment with a DPP-IV Inhibitor, NVP-DPP728, Increases Prandial Intact GPL-1 Levels and Reduces Glucose Exposure in Humans. Diabetes 2000, 49 (1), A39.
2. Truett G, Bahary N, Friedman J. M., Leibel RL. The Zucker rat obesity gene fatty (fa) maps to chromosome 5 and is a homologue of the mouse diabetes (db) gene. Proc Natl Acad Sci USA. 1991, 88, 7806–7809.
3. McIntosh, C. H. S.; Pederson, R. A.; Noninsulin-Dependent Animal Models of Diabetes Mellitus. In Experimental Models of Diabetes. Edited by John H. McNeill, CRC Press LLC, 1999, 337–398.

In Vivo Assay Methods.

Male Zucker$^{fa/fa}$ rats (Harlan) weighing between 400 and 450 g were housed in a room that was maintained on a 12 h light /dark cycle and were allowed free access to normal rodent chow and tap water. The day before the experiment, the rats were weighed and divided into control and treated groups of six. Rats were fasted 17 h prior to the start of the study. On the day of the experiment, animals were dosed orally with vehicle (water) or DPP-IV inhibitors (3 μmol/kg) at −30 min. Two blood samples were collected at −30 and 0 min by tail bleed. Glucose (2 g/kg) was administered orally at 0 min. Additional blood samples were collected at 15, 30, 60, 90 and 120 min. Blood samples were collected into EDTA containing tubes from Starstedt. Plasma glucose was determined by Cobas Mira (Roche Diagnostics) by the glucose oxidation method.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound of formula (I)

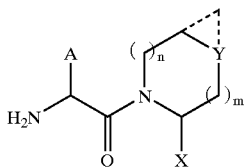

(I)

wherein:

n is 0, 1 or 2;

m is 0, 1 or 2;

the sum of n plus m is less then or equal to 2;

the dashed bonds forming a cyclopropyl ring when Y is CH;

X is hydrogen or CN;

Y is CH, CH$_2$, CHF, CF$_2$, O, S, SO, or SO$_2$

A is adamantyl which can be optionally substituted with from zero to six substituents each independently selected from OR$^1$, NR$^1$R$^2$, alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, aralkyl, heteroaryl, heteroarylalkyl, cycloheteroalkyl and cycloheteroalkylalkyl, all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

R$^1$ and R$^2$ are each independently selected from hydrogen, alkyl, alkenyl, alkynyl, aryl and heteroaryl;

including pharmaceutically acceptable salts thereof, and prodrug esters thereof, and all stereoisomers thereof, with the proviso that the compound of formula (I) is not selected from

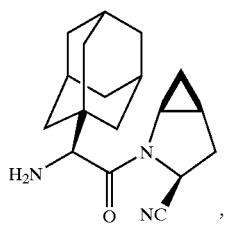
,
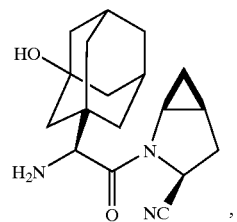
,

-continued
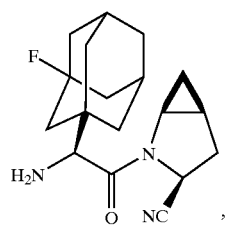 , and 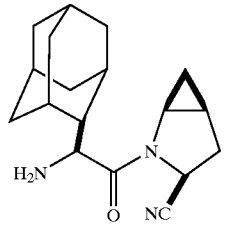 .
2. The compound as defined in claim 1 selected from
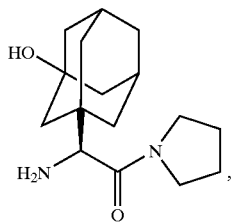 , 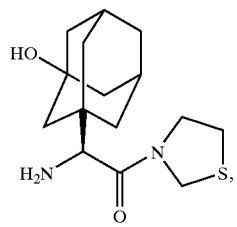 ,
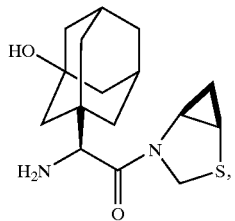 , 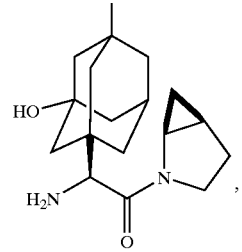 ,
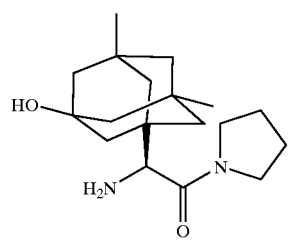 , 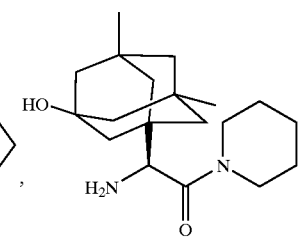 ,
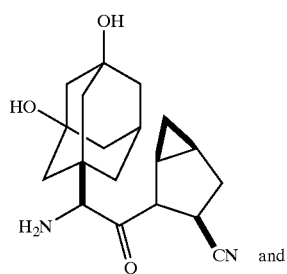 and 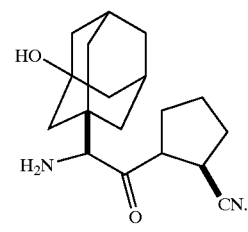 .
3. The compound as defined in claim 1 selected from
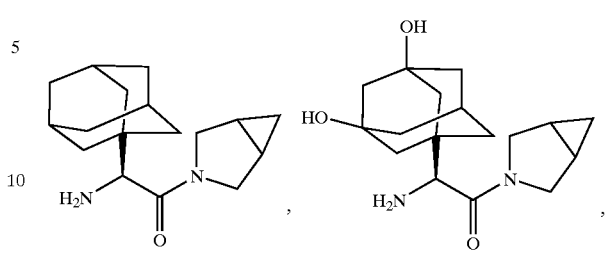 ,
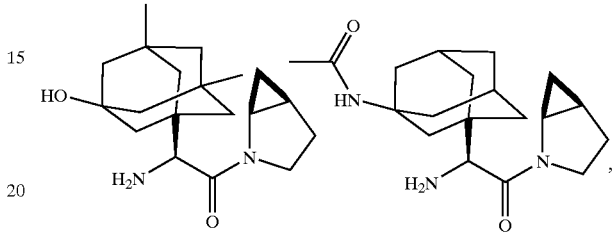 ,
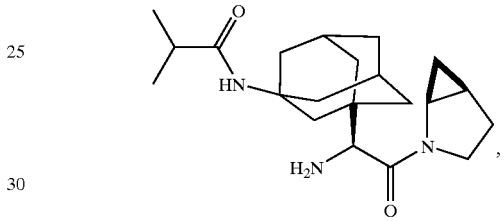 ,
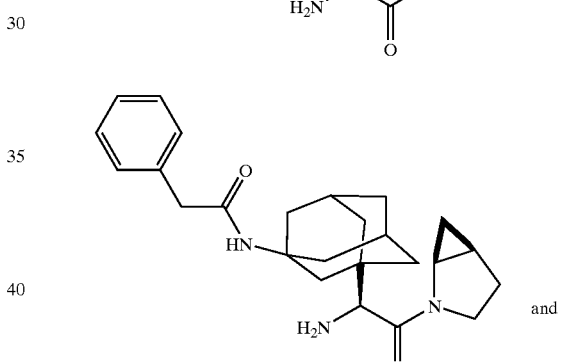 and
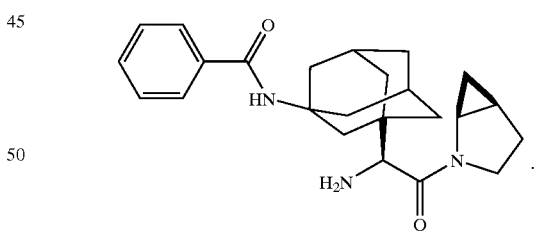 .
4. A compound of the formula
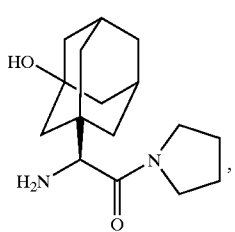 , 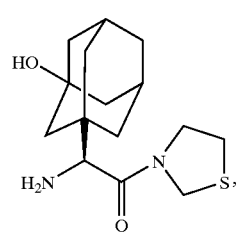 ,

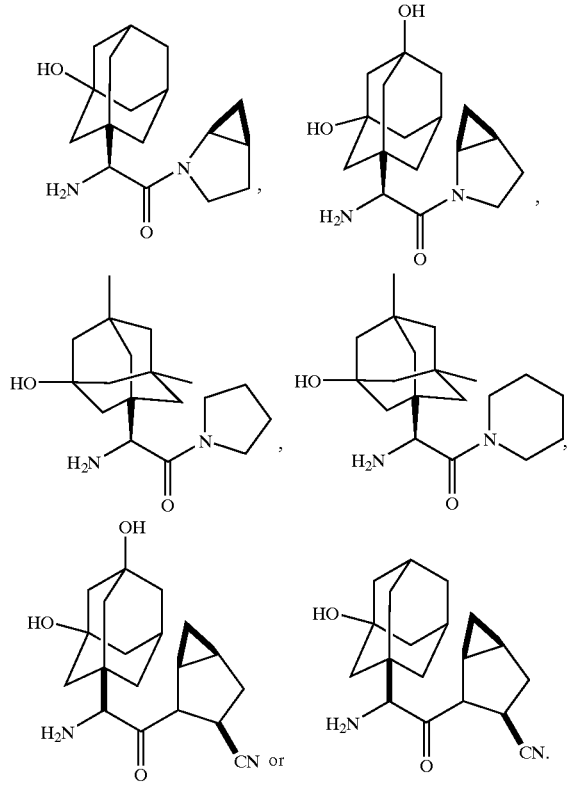
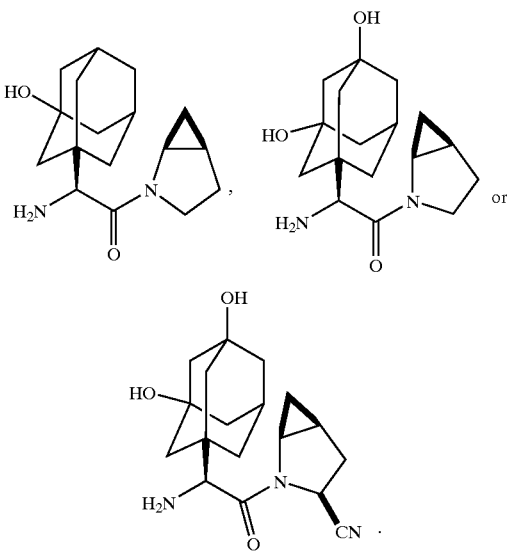
5. A compound of the formula
6. A pharmaceutical composition comprising a compound as defined in claim 1 and a pharmaceutically acceptable carrier therefor.
7. A pharmaceutical composition that inhibits DPP-IV containing a compound as defined in claim 1.
* * * * *

UNITED STATES PATENT AND TRADEMARK OFFICE
CERTIFICATE OF CORRECTION

PATENT NO. : 6,995,183 B2  Page 1 of 1
APPLICATION NO. : 10/899641
DATED : February 7, 2006
INVENTOR(S) : Lawrence G. Hamann et al.

It is certified that error appears in the above-identified patent and that said Letters Patent is hereby corrected as shown below:

Claim 2, Col. 49, lines 35 to 40, change the formula " 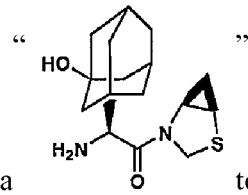 " to read

-- 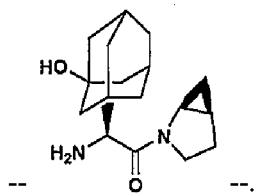 --.

Signed and Sealed this

Twenty-fifth Day of December, 2007

JON W. DUDAS
*Director of the United States Patent and Trademark Office*